US011738074B2

(12) United States Patent
Li

(10) Patent No.: US 11,738,074 B2
(45) Date of Patent: Aug. 29, 2023

(54) VACCINES AGAINST MALARIA TRANSMISSION

(71) Applicant: Jun Li, Miami, FL (US)

(72) Inventor: Jun Li, Miami, FL (US)

(73) Assignee: The Florida International University Board of Trustees, Miami, FL (US)

( * ) Notice: Subject to any disclaimer, the term of this patent is extended or adjusted under 35 U.S.C. 154(b) by 0 days.

(21) Appl. No.: 17/826,617

(22) Filed: May 27, 2022

(65) Prior Publication Data

US 2022/0296693 A1    Sep. 22, 2022

Related U.S. Application Data

(63) Continuation of application No. 17/072,394, filed on Oct. 16, 2020, now Pat. No. 11,351,238.

(60) Provisional application No. 62/916,009, filed on Oct. 16, 2019.

(51) Int. Cl.
*A61K 39/002* (2006.01)
*A61K 39/015* (2006.01)
*A61K 39/00* (2006.01)

(52) U.S. Cl.
CPC ...... *A61K 39/015* (2013.01); *A61K 2039/545* (2013.01); *A61K 2039/575* (2013.01)

(58) Field of Classification Search
None
See application file for complete search history.

(56) References Cited

U.S. PATENT DOCUMENTS 7,803,765 B2    9/2010    Watt et al.

FOREIGN PATENT DOCUMENTS

WO    2004074479 A1    9/2004

OTHER PUBLICATIONS

Decotiis, M., et al., "Identification of a novel plasmodium falciparum heat shock protein 70 (HSP70Z), also identified as CG4, as a transmission blocking vaccine candidate." American Jounral of Tropical Medicine and Hygiene (2014) 91:5 p. 495.
French, S., & Robson, B. "What is a conservative substitution?." Journal of molecular Evolution 19.2 (1983): 171-175.
Holloway S. P., et al. "Isolation of α-tubulin genes from the human malaria parasite, Plasmodium falciparum: sequence analysis of α-tubulin" Molecular Microbiology (1989) 3, pp. 1501-1510.
Katris, N.J., et al., "The Apical Complex Provides a Regulated Gateway for Secretion of Invasion Factors in Toxoplasma." PLoS Pathog, 2014, 10(4): e1004074, pp. 1-16.
Li, J., et al., "Genome-block expression-assisted association studies discover malaria resistance genes in Anopheles gambiae," PNAS, Dec. 2013, 110(51): 20675-20680.
Morrissette, N.S., et al., "Subpellicular microtubules associate with an intramembranous particle lattice in the protozoan parasite Toxoplasma gondii." Journal of Cell Science, 1997, 110: 35-42.
Motard, A., Motard, Annie, et al. "Immunization with the malaria heat shock like protein hsp70-1 enhances transmission to the mosquito." International immunology 7.1 (1995): 147-150.
Niu, G., et al., "Targeting mosquito FREP1 with a fungal metabolite blocks malaria transmission." Scientific Reports, 2015, 5(1): 1-18.
Niu, G., et al., "The fibrinogen-like domain of FREP1 protein is a broad-spectrum malaria transmission-blocking vaccine antigen." Journal of Biological Chemistry, 2017, 292(28): 11960-11969.
Santos, J.M., "Apicomplexan cytoskeleton and motors: Key regulators in morphogenesis, cell division, transport and motility." International Journal for Parasitology, 2009, 39: 153-162.
Tian, J.L., et al., "O-GlcNAcylation Regulates Primary Ciliary Length by Promoting Microtubule Disassembly." Science, 2019, 12: 379-391.
Wood. W., "Guide to molecular cloning techniques." vol. 152. (1987). Section IX. Chapter 49, pp. 443-457.
Zhang, G., et al., "Anopheles Midgut FREP1 Mediates Plasmodium Invasion." Journal of Biological Chemistry, 2015, 290(27): 16490-16501.
Nagel, S. D., & Boothroyd, J. C. "The α-and β-tubulins of Toxoplasma gondii are encoded by single copy genes containing multiple introns" Molecular and biochemical parasitology 29.2-3 (1988): 261-273.

*Primary Examiner* — Jennifer E Graser
(74) *Attorney, Agent, or Firm* — Saliwanchik, Lloyd & Eisenschenk

(57) ABSTRACT

The invention pertains to methods and vaccines suitable for preventing or reducing malaria transmission. The vaccines block the interaction between α-tubulin from a malarial parasite and FREP-1 from the mid-gut of a malaria carrier mosquito, for example, *Anopheles gambiae*.

17 Claims, 12 Drawing Sheets
(10 of 12 Drawing Sheet(s) Filed in Color)
Specification includes a Sequence Listing.

```
HA    1 M...CI...HVGGAGVG.GNACWLLYGL.HG.I.PDGQMPS..T IGGGD.S.. 51
PfA11 1 M.EV...HVGGAG..VGNACWLFCL.HG.I.PDGQMPS..A SRAN..AFN. 51

52 FFSETGAG..HVP.AVFVDLEPTV.D.V..TGT...QLF.P..L.TG..AA.. 102
 52 FFSETGAG..VP.CVFVDLEPTVVD.V..TGT...QLF.P..L.TG..AA.. 102

103 .A.GHY.IG.E.I.DLVL....I.KLA.QC..RL.GFLV.HS.GGG.G.GFTSLL 153
103 FA.GHY.IG.EV.DVCLD..I.KLA.NC..GL.GFLM.SAVGGG.GSGFGCLM 153

154 M..L.VD.G....LE.SI.PA.PGV..AVVEP....LT.T..TL..S.CAFMV 204
154 L..L.VD.G....LN.CCWPS.PGV..AVV.P..SVLS..S.LL.....VAIML 204

205 .NEAIY.IC..NLD.E..P.YNL....IS..IVSS.TASL.FDGAL.VDLT.. 255
205 .NEAIY.IC..NLD.E..P.YNL...IA.VISSL.TASL.FDGAL.VDV..F 255

256 ..LVF.P..I.FPLA..APVISA..AVH..LSVA..IT.NACF.PA.QMV..D 306
256 ..LVF.P..I.FMLSS.APVVSA..AVH..LSVS..IT..SAF.PA.MMA..D 306

307 PG.G..MACC.L..GDVVP.DVNAAIA.I..A..T.IQFVDWCP.GF..VG.. 357
307 P.HG..MACC.LM..GDVVP.DVNAAVA.I..A..T.IQFVDWCP.GF..CG.I. 357

358 .PP.VVPGGDLA..VQ..AVCML.S..TTA.A.AWA..LDH..FDLM.A...AFV.W. 408
358 .PP.VVPGGDLA..VM..AVCMI.SNS.A.A.EVF.S.MDQ.FDLM.A...AFV.W. 408

410 G.GM..GEF.S.A..EDMAAL....Y..VGV...V..G..G...GE.. - - 451
410 G.GM..GEF.S.A..EDLAAL....Y..VGI..SN.A..GE..GY.A.DY 453
```

FIG. 5A

```
Human              MRECISIHVGQAGVQIGNACWELYCLEHGIQPDGQMPSDKTIGGGDSFNTFFSETGAGK    60
P. vivax           MREVISIHVGQAGIQIGNACWELFCLEHGIQPDGQMPSDQVVAGGBDAFNTFFSETGAGK    60
P. knowlesi        MREVISIHVGQAGIQVGNACWELFCLEHGIQPDGQMPSDKAARANDDAFNTFFSETGAGK    60
P. malariae        MREVISIHVGQAGIQVGNACWELFCLEHGIQPDGQMPSDKAARANDDAFNTFFSETGAGK    60
P. falciparum NF54 MREVISIHVGQAGIQVGNACWELFCLEHGIQPDGQMPSDKASRANDDAFNTFFSETGAGK    60
P. falciparum 3D7  MREVISIHVGQAGIQVGNACWELFCLEHGIQPDGQMPSDKASRANDDAFNTFFSETGAGK    60
P. ovale           MREVISIHVGQAGIQVGNACWELFCLEHGIQPDGQMPSDKAARANDDAFNTFFSETGAGK    60
                   ***:******:***:*:*****:*********:*****:    .:**********

Human              HVPRAVFVDLEPTVIDEVRTGTYRQLFHPEQLITGKEDAANNYARGHYTIGKEIIDLVLD   120
P. vivax           HVPRCVFVDLEPTVVDEVRTGTYRQLFHPEQLISGKEDAANNFARGHYTIGKEVIDVCLD   120
P. knowlesi        HVPRCVFVDLEPTVVDEVRTGTYRQLFHPEQLISGKEDAANNFARGHYTIGKEVIDVCLD   120
P. malariae        HVPRCVFVDLEPTVVDEVRTGTYRQLFHPEQLISGKEDAANNFARGHYTIGKEVIDVCLD   120
P. falciparum NF54 HVPRCVFVDLEPTVVDEVRTGTYRQLFHPEQLISGKEDAANNFARGHYTIGKEVIDVCLD   120
P. falciparum 3D7  HVPRCVFVDLEPTVVDEVRTGTYRQLFHPEQLISGKEDAANNFARGHYTIGKEVIDVCLD   120
P. ovale           HVPRCVFVDLEPTVVDEVRTGTYRQLFHPEQLISGKEDAANNFARGHYTIGKEVIDVCLD   120
                   ****.*********:*****************:********:**********:***.**

Human              RIRKLADQCTRLQGFLVFHSFGGGTGSGFTSLLMERLSVDYGKKSKLEFSIYPAPQVSTA   180
P. vivax           RIRKLADNCTGLQGFLMFNAVGGGTGSGIGCLLERLAIDYGKKSKLNFCWPSPQVSTA    180
P. knowlesi        RIRKLADNCTGLQGFLMFSAVGGGTGSGFGCLMLERLSVDYGKKSKLNFCCWPSPQVSTA   180
P. malariae        RIRKLADNCTGLQGFLMFSAVGGGTGSGFGCLMLERLSVDYGKKSKLNFCCWPSPQVSTA   180
P. falciparum NF54 RIRKLADNCTGLQGFLMFSAVGGGTGSGFGCLMLERLSVDYGKKSKLNFCCWPSPQVSTA   180
P. falciparum 3D7  RIRKLADNCTGLQGFLMFSAVGGGTGSGFGCLMLERLSVDYGKKSKLNFCCWPSPQVSTA   180
P. ovale           RIRKLADNCTGLQGFLMFSAVGGGTGSGFGCLMLERLSVDYGKKSKLNFCCWPSPQVSTA   180
                   *:******:**.******:: *******:.**:**** :***********:* **.***

Human              VVEPYNSILTTHTTLEHSDCAFMVDNEAIYDICRRNLDIERPTYTNLNRLIGQIVSSITA   240
P. vivax           VVEPYNSVLSTHSLLEHTDVAIMLDNEAIYDICKRNLDIERPTYTNLNRLIAQVISSLTA   240
P. knowlesi        VVEPYNSVLSTHSLLEHTDVAIMLDNEAIYDICRRNLDIERPTYTNLNRLIAQVISSLTA   240
P. malariae        VVEPYNSVLSTHSLLEHTDVAIMLDNEAIYDICRRNLDIERPTYTNLNRLIAQVISSLTA   240
P. falciparum NF54 VVEPYNSVLSTHSLLEHTDVAIMLDNEAIYDICRRNLDIERPTYTNLNRLIAQVISSLTA   240
P. falciparum 3D7  VVEPYNSVLSTHSLLEHTDVAIMLDNEAIYDICRRNLDIERPTYTNLNRLIAQVISSLTA   240
P. ovale           VVEPYNSVLSTHSLLEHTDVAIMLDNEAIYDICRRNLDIERPTYTNLNRLIAQVISSLTA   240
                   *******:*:**: ***:*.*:*:*********:**********:****:*:****:**

Human              SLRFDGALNVDLTEFQTNLVPYPRIHFPLATYAPVISAEKAYHEQLSVAEITNACFEPAN   300
P. vivax           SLRFDGALNVDVTEFQTNLVPYPRIHFMLSSYAPIISAEKAYHEQLSVSEITNSAFEPAS   300
P. knowlesi        SLRFDGALNVDVTEFQTNLVPYPRIHFMLSSYAPVVSAEKAYHEQLSVSEITNSAFEPAN   300
P. malariae        SLRFDGALNVDVTEFQTNLVPYPRIHFMLSSYAPVVSAEKAYHEQLSVSEITNSAFEPAN   300
P. falciparum NF54 SLRFDGALNVDVTEFQTNLVPYPRIHFMLSSYAPVVSAEKAYHEQLSVSEITNSAFEPAN   300
P. falciparum 3D7  SLRFDGALNVDVTEFQTNLVPYPRIHFMLSSYAPVVSAEITNSAFEPAN             300
P. ovale           SLRFDGALNVDVTEFQTNLVPYPRIHFMLSSYAPVVSAEKAYHEQLSVSEITNSAFEPAN   300
                   ***********:**************** *:***::***:********.****.****.

Human              QTVKCDPGHGKYMACCLLYRGDVVPKDVNAAIATIKTKRTIQFVDWCPTGFKVGINYQPP   360
P. vivax           MMAKCDPRHGKYMACCIMYRGDVVPKDVNAAVATIKTKRSIQFVDWCPTGFKCGINYQPP   360
P. knowlesi        MMAKCDPRHGKYMACCIMYRGDVVPKDVNAAVATIKTKRTIQFVDWCPTGFKCGINYQPP   360
P. malariae        MMAKCDPRHGKYMACCIMYRGDVVPKDVNAAVATIKTKRTIQFVDWCPTGFKCGINYQPP   360
P. falciparum NF54 MMAKCDPRHGKYMACCIMYRGDVVPKDVNAAVATIKTKRTIQFVDWCPTGFKCGINYQPP   360
P. falciparum 3D7  MMAKCDPRHGKYMACCIMYRGDVVPKDVNAAVATIKTKRTIQFVDWCPTGFKCGINYQPP   360
P. ovale           MMAKCDPRHGKYMACCIMYRGDVVPKDVNAAVATIKTKRTIQFVDWCPTGFKCGINYQPP   360
                    :.****.********::**********************.*************.*****

Human              TVVPGGDLAKVQRAVCMLSNTTAIAEAWARLDHKFDLMYAKRAFVHWYVGEGMEEGEFSE   420
P. vivax           TVVPGGDLAKVMRAVCMISNSTAIAEVFSRMDQKFDLMYAKRAFVHWYVGEGMEEGEFSE   420
P. knowlesi        TVVPGGDLAKVMRAVCMISNSTAIAEVFSRMDQKFDLMYAKRAFVHWYVGEGMEEGEFSE   420
P. malariae        TVVPGGDLAKVMRAVCMISNSTAIAEVFSRMDQKFDLMYAKRAFVHWYVGEGMEEGEFSE   420
P. falciparum NF54 TVVPGGDLAKVMRAVCMISNSTAIAEVFSRMDQKFDLMYAKRAFVHWYVGEGMEEGEFSE   420
P. falciparum 3D7  TVVPGGDLAKVMRAVCMISNSTAIAEVFSRMDQKFDLMYAKRAFVHWYVGEGMEEGEFSE   420
P. ovale           TVVPGGDLAKVMRAVCMISNSTAIAEVFSRMDQKFDLMYAKRAFVHWYVGEGMEEGEFSE   420
                   *********** *****:**:*****.::*:*:**********************

Human              AREDMAALEKDYEEVGVDSVEGEGEEEGSEY--    451
P. vivax           AREDLAALEKDYEEVGIETNEGEGEDEGYE---    450
P. knowlesi        AREDLAALEKDYEEVGIETNEGEGEDEGYEAEY  453
P. malariae        AREDLAALEKDYEEVGIESNEGEGEDEGYDGEY  453
P. falciparum NF54 AREDLAALEKDYEEVGIESNEAEGEDEGYEADY  453
P. falciparum 3D7  AREDLAALEKDYEEVGIESNEAEGEDEGYEADY  453
P. ovale           AREDLAALEKDYEEVGIESNEGEGEDEGYEADY  453
                   ****:***********::: .*.***:*    *
```

FIG. 7

VACCINES AGAINST MALARIA TRANSMISSION

CROSS-REFERENCE TO RELATED APPLICATION

This application is a continuation application of U.S. Ser. No. 17/072,394, filed Oct. 16, 2020, which claims the benefit of U.S. Provisional Application Ser. No. 62/916,009, filed Oct. 16, 2019, both of which are hereby incorporated by reference herein in its entirety, including any figures, tables, and drawings.

GOVERNMENT SUPPORT

This invention was made with government support under AI125657 and AI115178 awarded by the National Institutes of Health and under 1453287 awarded by the National Science Foundation. The government has certain rights in the invention.

SEQUENCE LISTING

The Sequence Listing for this application is labeled "SeqList-15Oct20-ST25.txt," which was created on Oct. 15, 2019, and is 30 KB. The Sequence Listing is incorporated herein by reference in its entirety.

BACKGROUND OF THE INVENTION

Recent malaria campaigns, which were mainly achieved by distributing insecticide-treated bed-nets, have reduced malaria cases and deaths by 30% and 47% respectively since 2000. At present, malaria control is being challenged by the fast spread of insecticide-resistant mosquitoes, drug resistant parasites, and the lack of malaria vaccines. New approaches for malaria control are desperately needed.

The infection, differentiation, and development of *Plasmodium* in Anopheline mosquitoes are essential for malaria transmission. Thus, understanding the mechanisms of malaria transmission to mosquitoes will inform novel approaches for malaria control.

Human malaria is caused by five different *Plasmodium* species and transmitted by several *Anopheles* species. *P. falciparum* and *P. vivax* are responsible for 99% of malaria cases. Unlike most other diseases, *Plasmodium* development in Anopheline mosquitoes is essential for malaria transmission. When a mosquito takes blood from a malaria patient, haploid microgametes and macrogametes form diploid zygotes that transform into mobile ookinetes. Mobile ookinetes will overcome the physical barrier of the mosquito midgut including peritrophic matrix (PM) and endothelium sequentially to initiate the infection in mosquitoes.

A *Plasmodium* ookinete is asymmetric with an apical end and basal end. An invasive apparatus at the apical end secretes digestion enzymes to break the host midgut physical barriers for invasion. Thus, orienting and anchoring the ookinete apical end towards mosquito midgut epithelium is necessary for ookinete penetration of mosquito midgut peritrophic matrix and infection of endothelial cells. The apical polar complex is composed of tubulins and other proteins and undergoes dynamic cytoskeletal reorganization during *Plasmodium* invasion of host cells. *Plasmodium* tubulin proteins include α-tubulin-I, α-tubulin-II, and β-tubulin, while α-tubulin-II is a male-specific protein. Only α-tubulin-I and β-tubulin are expressed in diploid ookinetes.

Several interactions between a mosquito and parasites occur in the midgut before establishing infection. Each of these interactions is important for a productive infection. For instance, *Plasmodium vivax* Pvs25 binds to calreticulin, the mosquito midgut apical surface protein. The interaction between ookinete surface enolase and the mosquito midgut enolase-binding protein specifically mediates *P. berghei*, but not *P. falciparum*, to invade mosquitoes. However, none of these interactions are conserved across multiple species of *Plasmodium* and *Anopheles*.

Thus, the discovery of a conserved pathway for malaria transmission may provide a broad-spectrum target for interrupting malaria transmission through mosquitoes. Anti-malarial vaccine efforts have largely focused on merozoite surface proteins. However, vaccines based on merozoite antigens have had disappointing outcomes in clinical trials. By contrast, malaria transmission-blocking vaccines (TBV) have shown promising perspectives when considering the malaria transmission bottleneck in the mosquito midgut.

The fibrinogen-related protein 1 (FREP-1) gene was determined to have significant correlation with infection intensity of clinically circulating *P. falciparum* transmission to wild *Anopheles gambiae* in Kenya. Further investigation revealed that FREP1 was an essential component of the mosquito midgut peritrophic matrix that bound *P. falciparum* ookinetes to facilitate their invasion.

Further experiments using transgenic *An. gambiae* and transmission-blocking small molecule discovery approaches established the critical role of FREP1-mediated *Plasmodium* transmission. Notably, antibodies against FREP1 can inhibit multiple species of *Plasmodium* (e.g. *P. falciparum*, *P. vivax* and *P. berghei*) from invading multiple species of *Anopheles* (e.g. *An. gambiae* and *An. dirus*). Thus, the FREP1-mediated *Plasmodium* transmission pathway is highly conserved across *Plasmodium* and *Anopheles*. Previous experiments showed that FREP1 bound to *P. falciparum* and that FREP1 also bound to rodent malaria pathogen *P. berghei*.

Despite the importance of FREP1-mediated *Plasmodium* invasion pathway in Anopheline mosquitoes, the parasite-expressed FREP1-binding partners (FBPs) were unknown. Thus, there is a need for identifying FBPs and developing methods for disrupting *Plasmodium* transmission to mosquitoes. There is also a need to develop methods for preventing and reducing the transmission of malaria.

BRIEF SUMMARY OF THE INVENTION

The subject invention provides agents, methods and compositions that prevent or reduce the transmission of malaria. The agents, methods and compositions according to the subjection invention block the malaria transmission cycle by specifically reducing or eliminating the formation of malaria parasite oocysts in the carriers.

The subject invention also provides methods and compositions for treating a subject infected with malaria parasites or malaria parasite oocysts. The subject invention further provides methods and compositions for treating a subject suffering from malaria. In one embodiment, the malarial parasite is *P. vivax*, *P. knowlesi*, *P. malariae*, *P. falciparum*, or *P. ovale*.

In one embodiment, the subject may be any animal including mammals, preferably, human. The subjects further include, but are not limited to, non-human primates, rodents (e.g., rats, mice), dogs, cats, horses, cattle, pigs, sheep, goats, chickens, guinea pigs, hamsters and the like.

The subject invention provides agents that block the interaction between α-tubulin-1 from a malarial parasite and FREP-1 from the mid-gut of a malaria carrier mosquito. Blocking this interaction can be used according to the subject invention to prevent or reduce malaria transmission.

The blocking agent can be, for example, a protein, a carbohydrate, a nucleic acid, or an aptamer. Preferably, the agent is a protein, such as an antibody or an antigen binding fragment thereof.

The antibody or the antigen binding fragment thereof can specifically bind α-tubulin-1 from a malarial parasite while not binding or binding only minimally, to a human α-tubulin-1. Certain such antibodies, or the antigen binding fragments thereof, specifically bind to an epitope that is specific to the malaria parasite.

In one embodiment, the malaria transmission-blocking vaccine comprises an antigen from a malaria parasite that, when administered to a subject, induces the production, in the subject, of an agent that blocks the interaction between a mid-gut PM protein of a mosquito and the antigen from the malaria parasite.

In certain embodiments, the antigen may be selected from FBP1 (Hsp70), FBP3 (α-tubulin 1), FBP5 (U1 snRNA associated protein), and FBP6 (Exported protein IBIS1). In specific embodiments, the antigen comprises an amino acid sequence selected from SEQ ID NOs: 2-6 and amino acid sequences sharing at least 85%, 90%, 95%, 98% or 99% identity to any of SEQ ID NOs: 2-6.

In a preferred embodiment, the agent is an antibody, or the antigen binding fragment thereof, that specifically binds the antigen from the malaria parasite, the antigen preferably being Plasmodium α-tubulin-1. In a further embodiment, the antibody or the antigen binding fragment thereof specifically binds to a sequence selected from SEQ ID NOs: 2-6 and/or a sequence sharing at least 85%, 90%, 95%, 98% or 99% identity to any of SEQ ID NOs: 2-6. In a specific embodiment, the antibody or the antigen binding fragment thereof specifically binds to an epitope or an amino acid sequence comprising, or consisting of, a sequence of AARANDDAF (SEQ ID NO: 8), AARAN (SEQ ID NO: 9), QVVAGG (SEQ ID NO: 10), QVVAGGDDAF (SEQ ID NO: 11), ASRANDDA (SEQ ID NO: 42), MFSAV (SEQ ID NO: 43), NFCCWPSP (SEQ ID NO: 44), VFSRMDQK (SEQ ID NO: 45), and/or YEADY (SEQ ID NO: 7).

In a specific embodiment, the malaria transmission-blocking vaccine induces, in a host, the production of an agent that blocks the interaction between α-tubulin-1 from a malarial parasite and FREP-1 from the mid-gut of a malaria carrier mosquito.

Further embodiments of the invention provide a method of preventing or reducing transmission of malaria, comprising administering to a subject a vaccine composition that induces the production of an agent that blocks the interaction between α-tubulin-1 from a malarial parasite and FREP-1 from the mid-gut of a malaria carrier mosquito.

In one embodiment, the subject invention provides methods for reducing malaria transmission from a subject suffering from malaria, the method comprising administering to the subject the malaria transmission-blocking vaccine of the subject invention. Preferably, the malaria is caused by P. vivax, P. knowlesi, P. malariae, P. falciparum NF54, P. falciparum 3D7, or P. ovale. In a further embodiment, the method for reducing malaria transmission from a subject suffering from malaria further comprises administering to the subject one or more times of a boosting vaccine. Preferably, the boosting vaccine is the same as the transmission-blocking vaccine.

In one embodiment, the malaria transmission-blocking vaccine can be administered via oral, nasal, intramuscular, subcutaneous, or intravenous administration.

In one embodiment, the subject invention provides a method for preventing or reducing malaria transmission through a mosquito, comprising administering to the mosquito a malaria transmission-blocking agent comprising an antibody or antigen binding fragment thereof that specifically binds a FBP, e.g., Plasmodium α-tubulin-1. Preferably, the Plasmodium α-tubulin-1 comprises a sequence selected from SEQ ID NOs: 2-6 and/or a sequence sharing at least 85%, 90%, 95%, 98% or 99% identity to any of SEQ ID NOs: 2-6.

In one embodiment, the subject invention provides a method for blocking the invasion of a malaria parasite into the midguts of a mosquito, comprising administering to the mosquito a composition comprising a malaria transmission-blocking agent of the subjection invention.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIGS. 5A-5B show protein sequence comparison and purified Ab transmission-blocking assays. 5A) Sequence alignment of human α-tubulin (HA) (SEQ ID NO: 1) and *P. falciparum* α-tubulin-I (PfA) (SEQ ID NO: 5). 5B) Purified rabbit anti-human α-tubulin polyclonal Ab (labeled with α) significantly reduced the number of *P. falciparum* oocysts in *An. gambiae* midguts, while purified polyclonal Ab against human β-tubulin (labeled with β) did not inhibit *P. falciparum* transmission to *An. gambiae*. A non-related purified rabbit polyclonal Ab (anti-V5, labeled with control) was used as the negative control. Wilcoxon test was used to calculate P-value. The experiment was repeated, and the results were similar.

FIG. 7 shows the alignment of α-Tubulin homologs from humans (SEQ ID NO: 1) and several *Plasmodium* species: *P. vivax* (SEQ ID NO: 2), *P. knowlesi* (SEQ ID NO: 3), *P. malariae* (SEQ ID NO: 4), *P. falciparum* NF54 (SEQ ID NO: 5), *P. falciparum* 3D7 (SEQ ID NO: 5), and *P. ovale* (SEQ ID NO: 6).

BRIEF DESCRIPTION OF SEQUENCES

Figure 1A:
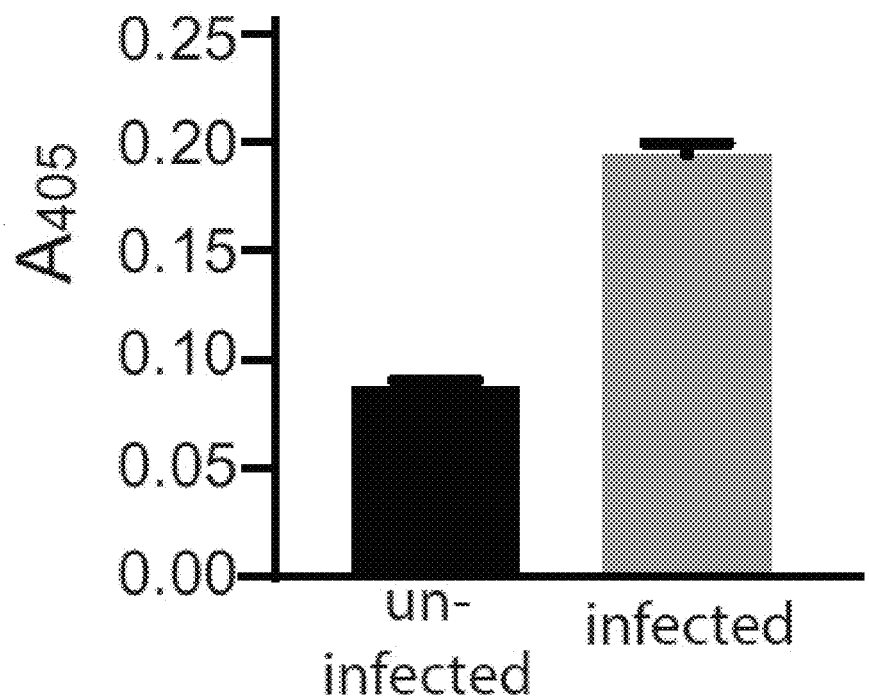
FIGS. 1A-1B show the determination of FREP1 binding to Plasmodium berghei parasites. 1A) FREP1 binds to P. berghei infected cells significantly higher than uninfected lysate (p<0.001). 1B) When the heat inactivated FREP1 protein or bovine serum album (BSA) replaced the functional FREP1, the binding between FREP1 and infected blood lysate disappeared.

SEQ ID NO: 1 is the amino acid sequence of a human α-tubulin contemplated for use according to the subject invention.

SEQ ID NO: 2 is the amino acid sequence of *P. vivax* α-tubulin contemplated for use according to the subject invention.

SEQ ID NO: 3 is the amino acid sequence of *P. knowlesi* α-tubulin contemplated for use according to the subject invention.

SEQ ID NO: 4 is the amino acid sequence of *P. malariae* α-tubulin contemplated for use according to the subject invention.

SEQ ID NO: 5 is the amino acid sequence of *P. falciparum* α-tubulin contemplated for use according to the subject invention.

SEQ ID NO: 6 is the amino acid sequence of *P. ovale* α-tubulin contemplated for use according to the subject invention.

SEQ ID NOs: 7-17 are amino acid sequences of *Plasmodium* α-tubulin-1 fragments contemplated for use according to the subject invention.

SEQ ID NOs: 18-19 are amino acid sequences of human α-tubulin-1 fragments contemplated for use according to the subject invention.

SEQ ID NO: 20 is a forward primer used to clone the *P. berghei* FBP genes contemplated for use according to the subject invention.

SEQ ID NO: 21 is a reverse primer used to clone the *P. berghei* FBP genes contemplated for use according to the subject invention.

SEQ ID NO: 22 is a forward primer used to clone the *P. berghei* FBP genes contemplated for use according to the subject invention.

SEQ ID NO: 23 is a reverse primer used to clone the *P. berghei* FBP genes contemplated for use according to the subject invention.

SEQ ID NO: 24 is a forward primer used to clone the *P. berghei* FBP genes contemplated for use according to the subject invention.

SEQ ID NO: 25 is a reverse primer used to clone the *P. berghei* FBP genes contemplated for use according to the subject invention.

SEQ ID NO: 26 is a forward primer used to clone the *P. berghei* FBP genes contemplated for use according to the subject invention.

SEQ ID NO: 27 is a reverse primer used to clone the *P. berghei* FBP genes contemplated for use according to the subject invention.

SEQ ID NO: 28 is a forward primer used to clone the *P. berghei* FBP genes contemplated for use according to the subject invention.

SEQ ID NO: 29 is a reverse primer used to clone the *P. berghei* FBP genes contemplated for use according to the subject invention.

SEQ ID NO: 30 is a forward primer used to clone the *P. berghei* FBP genes contemplated for use according to the subject invention.

SEQ ID NO: 31 is a reverse primer used to clone the *P. berghei* FBP genes contemplated for use according to the subject invention.

SEQ ID NO: 32 is a forward primer used to clone the *P. berghei* FBP genes contemplated for use according to the subject invention.

SEQ ID NO: 33 is a reverse primer used to clone the *P. berghei* FBP genes contemplated for use according to the subject invention.

SEQ ID NO: 34 is a forward primer used to clone the *P. berghei* FBP genes contemplated for use according to the subject invention.

SEQ ID NO: 35 is a reverse primer used to clone the *P. berghei* FBP genes contemplated for use according to the subject invention.

SEQ ID NO: 36 is a forward primer used to clone the *P. berghei* FBP genes contemplated for use according to the subject invention.

SEQ ID NO: 37 is a reverse primer used to clone the *P. berghei* FBP genes contemplated for use according to the subject invention.

SEQ ID NOs: 38-39 are primers used to amplify *P. falciparum* HSP70 contemplated for use according to the subject invention.

SEQ ID NOs: 40-41 are primers used to amplify *P. falciparum* α-tubulin 1 contemplated for use according to the subject invention.

SEQ ID NOs: 42-45 are amino acid sequences of *P. falciparum* α-tubulin 1 fragments contemplated for use according to the subject invention.

DETAILED DESCRIPTION OF THE INVENTION

The subject invention provides agents, methods and compositions that prevent or reduce the transmission of malaria. The agents and compositions according to the subjection invention block the malaria transmission cycle, preferably, by specifically reducing or eliminating the formation of malaria parasite oocysts in the carriers. The carrier may be an animal, such as a mammal, e.g., human, or an insect, e.g., mosquito.

The present invention also provides antigens, nucleic acid sequences and/or vectors encoding the antigens, and antibodies (and antibody-like molecules including aptamers and peptides) that specifically bind to the antigen, together with the uses thereof (either alone or in combination) in the prevention or the reduction of the transmission of malaria. In addition, this disclosure also provides targets for malaria control.

In certain embodiments, the malaria parasite is selected from *P. falciparum, P. malariae, P. ovale, P. vivax, P. knowlesi, P. berghei, P. chabaudi* and *P. yoelii*. In specific embodiments, malaria is caused by, for example, *Plasmodium* (P.) species including *P. falciparum, P. malariae, P. ovale, P. vivax, P. knowlesi, P. berghei, P. chabaudi* and *P. yoelii*.

In one embodiment, the subject invention provides transmission-blocking agents that block malaria transmission. Preferably, the transmission-blocking agents block the interaction between a midgut PM protein of a mosquito and one or more surface antigens of a malaria parasite. Blocking this interaction can be used according to the subject invention to prevent or reduce malaria transmission.

Preferably, the midgut PM protein is, for example, a mosquito FREP1 protein, and one or more surface antigens are FBPs on the surface of a malaria parasite. In a specific embodiment, the one or more FBPs are expressed at the apical end of the malaria parasite. Preferably, the one or more FBPs are expressed at the apical polar ring of the malaria parasite.

In specific embodiments, the FBPs is selected from FBP1 (Hsp70), FBP2 (RNA helicase DDXS), FBP3 (α-tubulin 1), FBP4 (EF-1 α), FBP5 (U1 snRNA associated protein), FBP6 (Exported protein IBIS1), FBP7, FBP8, and FBP9. Preferably, the FBPs are selected from FBP1 (Hsp70), FBP3 (α-tubulin 1), FBP5 (U1 snRNA associated protein), FBP6 (Exported protein IBIS1), FBP8, and FBP9. More preferably, the FBP is FBP3 (α-tubulin-I).

As described herein, nine *P. berghei* proteins were co-precipitated with FREP1-conjugated beads. After cloning these nine genes and expressing them in insect cells, six of them were confirmed to interact with FREP1 protein. Among them, α-tubulin 1 and heat shock protein 70 (Hsp70) were highly conserved in *Plasmodium* species with >95% identity. Specifically, this disclosure describes a FREP1-mediated *Plasmodium* invasion pathway in *Anopheles* midguts and identifies *Plasmodium* α-tubulin 1 as a FREP1 binding partner.

Accordingly, certain embodiments of the subject invention provide a transmission-blocking agent that blocks the interaction between α-tubulin-1 from a malarial parasite and FREP-1 from the mid-gut of a malaria carrier mosquito.

Non-limiting examples of α-tubulin-1 from malarial parasites include α-tubulin-1 from *P. vivax, P. knowlesi, P. malariae, P. falciparum* NF54, *P. falciparum* 3D7, or *P. ovale* (FIG. 7). Additional examples of α-tubulin-1 from malarial parasites are known in the art and such embodiments are within the purview of the invention.

Examples of FREP-1 from the mid-gut of a malaria carrier mosquito are known in the art and can be identified, for example, by searching protein databases.

In one embodiment, the transmission-blocking agent recognizes and binds one or more FBPs on the surface of the malaria parasites. The transmission-blocking agent may also reduce and/or inhibit the expression and/or function of one or more FBPs on the surface of the malaria parasites.

In specific embodiments, the transmission-blocking agent according to the subject invention can be, for example, a protein, a polypeptide, a carbohydrate, or a nucleic acid (e.g., siRNA, and aptamer). Preferably, the transmission-blocking agent is a protein or peptide, such as an antibody or an antigen binding fragment thereof.

As used herein, the term "nucleic acid" refers to a polymeric form of nucleotides of any length, either ribonucleotides or deoxyribonucleotides, or analogs thereof. This term refers to the primary structure of the molecule, and thus includes double- and single-stranded DNA, as well as double- and single-stranded RNA. It also includes modified nucleic acids such as methylated and/or capped nucleic acids, nucleic acids containing modified bases, backbone modifications, and the like. The terms "nucleic acid" and "nucleotide sequence" are used interchangeably.

As used herein, the term "antibody" refers to polypeptide molecules which are capable of binding an epitope or antigenic determinant, e.g., non-covalently, and reversibly. For example, a naturally occurring IgG antibody is a tetramer comprising at least two heavy (H) chains and two light (L) chains inter-connected by disulfide bonds. Each heavy chain is comprised of a heavy chain variable region (abbreviated herein as VH) and a heavy chain constant region. The heavy chain constant region is comprised of three domains, CH1, CH2 and CH3. Each light chain is comprised of a light chain variable region (abbreviated herein as VL) and a light chain constant region. The light chain constant region is comprised of one domain, CL. The VH and VL regions can be further subdivided into regions of complementarity determining regions (CDR), interspersed with regions of framework regions (FR). Each VH and VL is composed of, for example, three CDRs and four FRs arranged from N-terminus to C-terminus. The variable regions of the heavy and light chains contain a binding domain that interacts with an antigen. The constant regions of the antibodies may mediate the binding of the immunoglobulin to host tissues or factors. The antibodies can be from any animal origin including birds and mammals. Preferably, the antibodies are mammalian e.g. human, rat, mouse, murine, rabbit, goat, guinea pig, camel, horse and the like, or other suitable animals e.g. chicken.

The phrase "antigen binding fragment" as used herein refers to the antigen binding portion of an antibody, such as Fab, Fab' and F(ab')2, and Fd. Other antigen binding fragments include single-chain antibodies, disulfide-linked Fvs (sdFv), variable fragment (Fv), single chain variable fragment (scFv), variable domain of heavy chain antibodies (VHH), and fragments comprising either a VL or VH domain. Further examples of antigen binding fragments include monovalent forms of antigen binding fragments that contain the antigen binding site include single chain Fab fragment (scFab), single domain antibody (sdAbs), Shark Variable New Antigen Receptor (VNAR) or Variable Lymphocyte Receptors (VLRs). Furthermore, non-antibody scaffolds such as affimers, affibodies, darpins, anticalins, monobodies are also examples of an "antigen binding fragment." Additional examples of antigen binding fragments are well known in the art and uses of such antigen binding fragments are within the purview of the instant invention.

The antibodies can be monoclonal antibodies, polyclonal antibodies, chimeric antibodies, or humanized antibodies. The antibodies can be of any type/class (e.g., IgG, IgE, IgM, IgD, IgA and IgY), or subclass (e.g., IgG1, IgG2, IgG3, IgG4, IgA1 and IgA2). Additional examples of antibodies are known in the art and such embodiments are within the purview of the invention.

In one embodiment, the antibody or the antigen binding fragment thereof can specifically bind a FBP from the malaria parasite. The FBP can be selected from, for example, FBP1 (Hsp70), FBP2 (RNA helicase DDXS), FBP3 (α-tubulin 1), FBP4 (EF-1 α), FBP5 (U1 snRNA associated protein), FBP6 (Exported protein IBIS1), FBP7, FBP8, and FBP9.

In a specific embodiment, the antibody or the antigen binding fragment thereof can specifically bind α-tubulin-1 from a malarial parasite while not binding or binding only minimally, to a human α-tubulin-1. Certain such antibodies, or the antigen binding fragments thereof, specifically bind to an epitope that is specific to the malaria parasite.

In one embodiment, the antibody or the antigen binding fragment thereof specifically binds to a sequence comprising, or consisting of, any of SEQ ID NOs: 2-6, fragments and variants thereof, and/or a sequence sharing at least 85%, 86%. 87%, 88%, 89%, 90%, 91%, 92%, 93%, 94%, 95%, 96%, 97%, 98%, 99%, 99.5%, or 99.9% identity to any of SEQ ID NOs: 2-6 and fragments and variants thereof.

As use herein, the term "fragment" refers to amino acid or nucleic acid sequences that are not full-length amino acid or nucleic acid sequences and that do not significantly affect or alter the binding characteristics of the antibody. The fragment may comprise at least 5, 10, 15, 20, 25, 30, 35, 40, 45, 50, 55, 60, 65, 70, 75, 80, 85, 90, 95, or 100 consecutive amino acids or nucleotides of the full-length amino acid or nucleic acid sequences. As use herein, the term "variant" refers to amino acid or nucleic acid sequences modified to yield a functionally equivalent molecule. Such modifications include, for example, individual substitution, deletion or addition to a polypeptide sequence or a nucleic acid sequence, and two or more substitutions, deletions and/or additions to a polypeptide sequence or a nucleic acid sequence. Such variants are in addition to and do not exclude polymorphic variants, interspecies homologs, orthologs, and alleles.

As used herein, the term "specifically binds," "specifically binding" "selectively binds" or "selectively binding," when used in the context of describing the interaction between an antigen (e.g., a protein) and an antibody, antibody fragment, antigen binding fragment or variant thereof, refers to a binding reaction that is determinative of the presence of the antigen in a heterogeneous population of proteins and other biologics, e.g., in a biological sample, e.g., a blood, serum, plasma or tissue sample. Thus, the antibodies, antibody fragments, antigen binding fragments or variants thereof, with a particular binding specificity bind to a particular antigen at least 2, 3, 4, 5, 6, 7, 8, 9, or 10 times the background and do not substantially bind in a significant amount to other antigens present in the sample.

In one embodiment, the antibody or the antigen binding fragment thereof specifically binds to an epitope or an amino acid sequence comprising, or consisting of, a sequence of AARANDDAF (SEQ ID NO: 8) and/or AARAN (SEQ ID NO: 9). The antibody or antigen binding fragment thereof may also bind to an epitope or an amino acid sequence comprising, or consisting of, a sequence of QVVAGG (SEQ ID NO: 10) and/or QVVAGGDDAF (SEQ ID NO: 11).

In one embodiment, the antibody or the antigen binding fragment thereof specifically binds to an epitope or an amino acid sequence comprising, or consisting of, a sequence of

```
                                     (SEQ ID NO: 12)
            STHSLLEHTDVAI, (SEQ ID NO: 13)
            IETNE, (SEQ ID NO: 14)
            ASRANDDAF (SEQ ID NO: 15)
            ASRAN, (SEQ ID NO: 16)
            AEVFSRMDQKFD,
            and/or (SEQ ID NO: 17)
            FGCLMLERLSVDYG.
```

In one embodiment, the antibody or the antigen binding fragment thereof specifically binds to an epitope or an amino acid sequence comprising, or consisting of, a sequence of ASRANDDA (SEQ ID NO: 42), MFSAV (SEQ ID NO: 43), NFCCWPSP (SEQ ID NO: 44), VFSRMDQK (SEQ ID NO: 45), and/or YEADY (SEQ ID NO: 7).

In one embodiment, the antibody or the antigen binding fragment thereof recognize one or more regions on α-tubulin-1. In a specific embodiment, the one or more regions are selected from AARANDDAF (SEQ ID NO: 8), AARAN (SEQ ID NO: 9), QVVAGG (SEQ ID NO: 10), QVVAGGDDAF (SEQ ID NO: 11), STHSLLEHTDVAI (SEQ ID NO: 12), IETNE (SEQ ID NO: 13), ASRANDDAF (SEQ ID NO: 14), ASRAN (SEQ ID NO: 15), AEVFSRMDQKFD (SEQ ID NO: 16), FGCLMLERLSVDYG (SEQ ID NO: 17), ASRANDDA (SEQ ID NO: 42), MFSAV (SEQ ID NO: 43), NFCCWPSP (SEQ ID NO: 44), VFSRMDQK (SEQ ID NO: 45), and YEADY (SEQ ID NO: 7). Preferably, the one or more regions are selected from ASRANDDA (SEQ ID NO: 42), MFSAV (SEQ ID NO: 43), NFCCWPSP (SEQ ID NO: 44), VFSRMDQK (SEQ ID NO: 45), and YEADY (SEQ ID NO: 7).

In another embodiment, the antibody or the antigen binding fragment thereof does not bind to an epitope or an amino acid sequence comprising, or consisting of, a sequence of TIGGGDDS (SEQ ID NO: 18) or TIGGG (SEQ ID NO: 19).

In one embodiment, the antibody or the antigen binding fragment thereof specifically binds to one or more epitopes or amino acid sequences comprising a sequence selected from SEQ ID NOs: 7-17 and 42-45.

In one embodiment, the antibody or antigen binding fragment thereof can be produced by administering to a subject one or more FBPs of malaria parasite and optionally with compounds that stimulate the immune system of the subject to produce antibodies or antigen binding fragments thereof against the administered one or more FBPs. Further details of producing polyclonal antibodies, monoclonal antibodies, chimeric antibodies, or humanized antibodies from such animals are known in the art and can be readily practiced to produce the antibodies of the claimed invention.

In a specific embodiment, the antibody or an antigen binding fragment thereof can be produced by administering to a mammal an α-tubulin-1 protein from a malarial parasite (for example, α-tubulin-1 provided in FIG. 7) or a fragment thereof, preferably, along with one or more compounds that stimulate the mammal's immune system to produce antibodies against the administered protein.

In preferred embodiments, the antibody that blocks the interaction between α-tubulin-1 from a malarial parasite and FREP-1 from the mid-gut of a malaria carrier mosquito specifically binds α-tubulin-1 from a malarial parasite while not binding or binding only minimally, to a human α-tubulin-1. A person of ordinary skill in the art can readily produce such antibodies, for example, by using the sequence alignment provided in FIG. 7 to identify an epitope that is present in an α-tubulin-1 from a malarial parasite and absent in a human α-tubulin-1.

In a specific embodiment, the antibody or antigen binding fragment thereof comprises A-3 or A-16. Preferably, the antibody or antigen binding fragment thereof is A-3 or A-16.

The antibodies or antigen binding fragments, and variants thereof have a minimally binding affinity to human α-tubulin-1, for example, with a $K_D$ (M) ranging from about $1 \times 10^{-3}$ to about $1 \times 10^{-6}$, from about $5 \times 10^{-3}$ to about $5 \times 10^{-5}$, from about $1 \times 10^{-4}$ to about $1 \times 10^{-5}$, or from about $5 \times 10^{-4}$ to about $1 \times 10^{-5}$. The antibodies or antigen binding fragments, and variants thereof have a binding affinity to α-tubulin-1 from a malarial parasite, for example, with a $K_D$ (M) ranging from about $5 \times 10^{-6}$ to about $1 \times 10^{-13}$, from about $1 \times 10^{-7}$ to about $1 \times 10^{-13}$, from about $5 \times 10^{-7}$ to about $5 \times 10^{-12}$, from about $1 \times 10^{-8}$ to about $1 \times 10^{-12}$, from about $5 \times 10^{-8}$ to about $5 \times 10^{-11}$, from about $1 \times 10^{-9}$ to about $5 \times 10^{-11}$, from about $5 \times 10^{-9}$ to about $1 \times 10^{-11}$, from about $1 \times 10^{-7}$ to about $1 \times 10^{-10}$, from about $1 \times 10^{-7}$ to about $1 \times 10^{-9}$, from about $5 \times 10^{-7}$ to about $1 \times 10^{-9}$, or from about $1 \times 10^{-10}$ to about $1 \times 10^{-11}$.

In one embodiment, the transmission-blocking agent may be an antiserum against one or more FBPs on the surface of the malaria parasites. Preferably, the transmission-blocking agent is an antiserum against at least one of FBP1 (Hsp70), FBP2 (RNA helicase DDXS), FBP3 (α-tubulin 1), FBP4 (EF-1 α), FBP5 (U1 snRNA associated protein), FBP6 (Exported protein IBIS1), FBP7, FBP8, and FBP9. More preferably, the transmission-blocking agent is an antiserum against α-tubulin 1 and/or Hsp70 of the malaria parasite. Antisera against α-tubulin 1 and Hsp70 were produced in mice to determine their effects on Plasmodium transmission. Anti-serum against P. falciparum α-34 tubulin 1 significantly inhibited P. falciparum transmission to An. gambiae.

In one embodiment, the subject invention provides an antigen or a nucleic acid sequence encoding the antigen that can stimulate an immune response once administered into a subject to produce an antibody or antigen binding fragment thereof against the antigen. Preferably, the antigens are FBPs on the surface of a malaria parasite. In specific embodiments, the FBPs are selected from FBP1 (Hsp70), FBP2 (RNA helicase DDXS), FBP3 (α-tubulin 1), FBP4 (EF-1 α), FBP5 (U1 snRNA associated protein), FBP6 (Exported protein IBIS1), FBP7, FBP8, and FBP9. Preferably, the FBPs is selected from FBP1 (Hsp70), FBP3 (α-tubulin 1), FBP5 (U1 snRNA associated protein), FBP6 (Exported protein IBIS1), FBP8, and FBP9.

In a preferred embodiment, the FBP is FBP3 (α-tubulin-I) having an amino acid sequence comprising, or consisting of, any of SEQ ID NOs: 2-6, fragments and variants thereof, and/or an amino acid sequence sharing at least 85%, 86%. 87%, 88%, 89%, 90%, 91%, 92%, 93%, 94%, 95%, 96%, 97%, 98%, 99%, 99.5%, or 99.9% identity to any of SEQ ID NOs: 2-6 and fragments and variants thereof.

The antigen used for the present invention can be modified polypeptide derived from a naturally occurring protein. The modified polypeptide may be a fragment of the naturally occurring protein. In one embodiment, the modified polypeptide has at least 70%, 75%, 80%, 85%, 90%, 91%, 92%, 93%, 94%, 95%, 96%, 97%, 98%, 99%, 99.5%, or 99.9% amino acid sequence identity to a polypeptide derived from a naturally occurring protein. In one embodiment, the modified polypeptide derived is a mutant where at most 10% of the amino acids are deleted, substituted, and/or added based on a polypeptide derived from naturally occurring protein.

In one embodiment, the subject invention also provides a composition comprising the antigen or the nucleic acid sequence encoding the antigen of the subject invention, and a pharmaceutically acceptable carrier. In one embodiment, the composition comprises one or more antigens or nucleic acid sequences encoding one or more antigens of the subject invention, and a pharmaceutically acceptable carrier.

"Pharmaceutically acceptable carrier" refers to a diluent, adjuvant or excipient with which the antigen disclosed herein can be formulated. Typically, a "pharmaceutically acceptable carrier" is a substance that is non-toxic, biologically tolerable, and otherwise biologically suitable for administration to a subject, such as an inert substance, added to a pharmacological composition or otherwise used as a diluent, or excipient to facilitate administration of the antigen disclosed herein and that is compatible therewith. Examples of excipients include various sugars and types of starches, cellulose derivatives, gelatin, vegetable oils, and polyethylene glycols. Additional examples of carriers suitable for use in the pharmaceutical compositions are known in the art and such embodiments are within the purview of the invention.

In a specific embodiment, the composition comprises Plasmodium α-tubulin-1 or nucleic acid sequences encoding Plasmodium α-tubulin-1, and a pharmaceutically acceptable carrier. In a specific embodiment, Plasmodium α-tubulin-1 has a sequence selected from SEQ ID NOs: 2-6 and sequences sharing at least 85%, 86%. 87%, 88%, 89%, 90%, 91%, 92%, 93%, 94%, 95%, 96%, 97%, 98%, 99%, 99.5%, or 99.9% identity to any of SEQ ID NOs: 2-6.

In one embodiment, the subject invention provides a composition for blocking malaria transmission comprising one or more malaria transmission-blocking agents according the subject invention. The composition may further comprise a pharmaceutically acceptable carrier.

In one embodiment, the subject invention also provides a malaria transmission-blocking vaccine that induces, in a host, the production of an agent that blocks the interaction between FBPs on the surface of malaria parasites and a mid-gut PM protein of a mosquito. Preferably, the malaria transmission-blocking vaccine, when administered to a subject, induces, in the subject, the production of an agent that blocks the interaction between α-tubulin-1 from a malarial parasite and FREP-1 from the mid-gut of a mosquito.

The agents discussed above, particularly, the antibodies or fragments thereof, that blocks the interaction between α-tubulin-1 from a malaria parasite and FREP-1 from the mid-gut of a malaria carrier mosquito can be used in the malaria transmission-blocking vaccines of the invention.

In one embodiment, the malaria transmission-blocking vaccine comprises a composition according to the subject invention. Preferably, the malaria transmission-blocking vaccine comprises one or more antigens of the subject invention or the nucleic acid sequences encoding one or more antigens of the subject invention, and a pharmaceutically acceptable carrier.

Specifically, the vaccine comprises the antigen, and a pharmaceutically acceptable carrier/adjuvant. Preferably, the agent is an antibody or the antigen binding fragment thereof that can specifically bind to α-tubulin-1 of a malarial parasite, or FREP-1 of a malaria carrier mosquito. Examples of adjuvant include, but are not limited to, aluminium salts, sodium hydroxide, Freund's complete adjuvant, Freund's incomplete adjuvant and Ribi solution.

The composition or vaccine provided in the present invention may contain a buffering agent such as dibasic sodium phosphate hydrate, sodium dihydrogen phosphate and sodium chloride; and preserving agent such as thimerosal.

The malaria transmission-blocking vaccines or compositions of the invention can be formulated for administration to a subject via any convenient and effective route, such oral, rectal, nasal, topical, (including buccal and sublingual), transdermal, vaginal, parenteral (including intramuscular, subcutaneous, and intravenous), spinal (epidural, intrathecal), and central (intracerebroventricular).

The subject invention also provides methods and compositions for treating a subject infected with malaria parasites or malaria parasite oocysts. The subject invention further provides methods and compositions for treating a subject suffering from malaria.

Further provided in the subject invention are methods of preventing or reducing malaria transmission from a subject infected with a malarial parasite, comprising administering to the subject a transmission-blocking agent that blocks the interaction between an antigen of a malarial parasite and FREP-1 from the mid-gut of a mosquito. Upon administration to a subject suffering from malaria, the agents disclosed herein would bind to the malarial parasites in the subject. If a mosquito bites the subject, the malarial parasites that enter the mid-gut of the mosquito would not be able to bind to the FREP-1 protein in the mid-gut of the mosquito and, thus, would not be able to continue their life cycle. As a result, transmission of malaria from the subject would be blocked.

In one embodiment, the method of preventing or reducing malaria transmission from a subject infected with a malarial parasite comprises administering to the subject a transmission-blocking agent that blocks the interaction between α-tubulin-1 from a malarial parasite and FREP-1 from the mid-gut of a malaria carrier mosquito.

The agents discussed above, particularly, the antibodies or fragments thereof, that blocks the interaction between α-tubulin-1 from a malaria parasite and FREP-1 from the mid-gut of a malaria carrier mosquito can be used in the methods of the invention. These agents can be administered on their own or can be produced by the administration of malaria transmission-blocking vaccines discussed above.

In one embodiment, the method for preventing or reducing malaria transmission from a subject infected with a malaria parasite comprises administering to the subject a transmission-blocking composition of the subject invention or a transmission-blocking vaccine that induces, in the subject, the production of an agent that blocks the interaction between FBPs on the surface of malaria parasites and a midgut PM protein of a mosquito. Preferably, the malaria transmission-blocking vaccine, when administered to a subject, induces, in the subject, the production of an agent that blocks the interaction between α-tubulin-1 from a malarial parasite and FREP-1 from the midgut of a mosquito.

In one embodiment, the subject invention also provides methods and compositions for immunizing a subject to stop the transmission of malaria parasites from the subject to a mosquito the method comprising administering to the subject a composition of the subject invention or a transmission-blocking vaccine.

In one embodiment, the subject invention provides a method for preventing or reducing the transmission of malaria through a mosquito by interrupting the infection, differentiation and/or development of a malaria parasite in the mosquito. Preferably, the method for preventing or reducing the transmission of malaria through a mosquito interrupts the infection of a malaria parasite in the mosquito.

In one embodiment, the method for preventing or reducing the transmission of malaria through a mosquito comprises feeding the mosquito/administering into the mosquito a composition comprising the malaria transmission-blocking agent according to the subject invention.

In some embodiments, the infection of a malaria parasite in the mosquito may be interrupted by blocking the invasion of the malaria parasite into the midgut of the mosquito; inhibiting the penetration of the malaria parasite through the midgut PM; and/or blocking the recognition between the malaria parasite and the midgut PM.

In one embodiment, the subject invention provides a method for reducing or inhibiting the infection of a malaria parasite in a mosquito, the method comprising feeding the mosquito/administering into the mosquito a composition comprising the malaria transmission-blocking agent according to the subject invention.

In one embodiment, the subject invention provides a method for blocking the invasion of a malaria parasite into the midgut of a mosquito, the method comprising feeding the mosquito/administering into the mosquito a composition comprising the malaria transmission-blocking agent according to the subject invention.

In one embodiment, the subject invention provides a method for inhibiting the interaction between a midgut PM protein of a mosquito and one or more surface antigens of a malaria parasite in the mosquito, the method comprising feeding the mosquito/administering into the mosquito a composition comprising the malaria transmission-blocking agent according to the subject invention. Preferably, the midgut PM protein is mosquito FREP1 protein and one or more surface antigens are FBPs on the surface of a malaria parasite. In a specific embodiment, the one or more FBPs are expressed at the apical end of the malaria parasite. Preferably, the one or more FBPs are expressed at the apical polar ring of the malaria parasite.

In preferred embodiments, the FBPs is selected from FBP1 (Hsp70), FBP3 (α-tubulin 1), FBP5 (U1 snRNA associated protein), FBP6 (Exported protein IBIS1), FBP8, and FBP9. More preferably, the FBP is FBP3 (α-tubulin-I).

In one embodiment, the subject invention provides a method for inhibiting the interaction between a midgut PM protein of a mosquito and one or more surface antigens of a malaria parasite, the method comprising contacting one or more surface antigens of the malaria parasite with a composition comprising the malaria transmission-blocking agent according to the subject invention.

In one embodiment, the subject invention provides a method for inhibiting, or reducing the amount of malaria oocytes in the mosquito, the method comprising feeding the mosquito/administering into the mosquito a composition comprising the malaria transmission-blocking agent according to the subject invention.

In one embodiment, the subject invention provide a method for producing an antiserum against one or more FBPs, the method comprising providing one or more FBPs, preferably, purified; immunizing a subject with one or more FBPs; optionally, repeating the step of immunizing the subject to provide multiple boosts; and obtaining the serum from the subject.

In one embodiment, the subject invention provides a method for preventing or reducing the transmission of malaria through a mosquito by using the antiserum produced according to the subject invention.

In one embodiment, the subject invention provides methods and compositions for reducing the malaria transmission rate in a population, the method comprising administering the transmission-blocking vaccine into the population. In a further embodiment, the population may or may not be suffering from malaria or has been diagnosed with malaria.

In one embodiment, the subject invention provides methods for treating malaria comprising administering in a subject an agent that blocks the interaction between α-tubulin-1 from a malaria parasite and FREP-1 from the mid-gut of a malaria carrier mosquito.

The subject invention provides methods for treating malaria comprising administering in a subject an antigen that induces the production of an agent that blocks the interaction between α-tubulin-1 from a malaria parasite and FREP-1 from the midgut of a malaria carrier mosquito.

Administration of the antigen, composition, transmission-blocking agents, and/or vaccine hereof can be performed using standard routes of administration. Non-limiting embodiments include parenteral administration, such as by injection, e.g., into the blood stream, intradermal, intramuscular, etc., or mucosal administration, e.g., intranasal, oral, and the like. In one embodiment, the vaccine is administered by intramuscular injection into the deltoid muscle. The skilled person knows the various possibilities to administer a vaccine hereof, in order to induce an immune response to the antigen(s) in the vaccine.

In certain embodiments, the vaccine hereof may be administered to a subject once the subject has been diagnosed with malaria. In certain embodiments, the vaccine of the subject invention may be administered to the subject one or more times. The first boosting vaccine may be administered within about 2 weeks to 2, 3, 4, 5, 6, 7, 8, 9, 10, 11, or 12 months after first administering the vaccine to the subject. In other embodiments, the first boosting vaccine is administered between about 4 and 24 months after administering the vaccine. In a further embodiment, the first boosting vaccine may be administered between about 2 and 20 years, between about 2 and 15 years, between about 2 and 10 years, or between about 2 and 5 years after the administration of the vaccine to the subject.

In certain embodiments, the second boosting vaccine may be administered within about 2 weeks to 2, 3, 4, 5, 6, 7, 8, 9, 10, 11, or 12 months after administering the first boosting vaccine. In other embodiments, the second boosting vaccine may be administered between about 4 and 24 months after administering the first boosting vaccine. In a further embodiment, the second boosting vaccine may be administered between about 2 and 20 years, between about 2 and 15 years, between about 2 and 10 years, or between about 2 and 5 years after the administration of the first boosting vaccine to the subject As used herein, the singular forms "a," "an," and "the" are intended to include the plural forms as well, unless the context clearly indicates otherwise. Further, to the extent that the terms "including," "includes," "having," "has," "with," or variants thereof are used in either the detailed description and/or the claims, such terms are intended to be inclusive in a manner similar to the term "comprising." The transitional terms/phrases (and any grammatical variations thereof) "comprising," "comprises," "comprise," include the phrases "consisting essentially of," "consists essentially of," "consisting," and "consists."

The transitional term "comprising," "comprises," or "comprise" is inclusive or open-ended and does not exclude additional, unrecited elements or method steps. By contrast, the transitional phrase "consisting of" excludes any element, step, or ingredient not specified in the claim. The phrases "consisting" or "consists essentially of" indicate that the claim encompasses embodiments containing the specified materials or steps and those that do not materially affect the basic and novel characteristic(s) of the claim. Use of the term "comprising" contemplates other embodiments that "consist" or "consisting essentially of" the recited component(s).

The term "about" means within an acceptable error range for the particular value as determined by one of ordinary skill in the art, which will depend in part on how the value is measured or determined, i.e., the limitations of the measurement system. Typically, "about" indicates within a range of 0 to 10% of a given value. For example, when term "about" is used in the context of the number of nucleotides in oligonucleotides; these oligonucleotides contain the stated number of nucleotides with a variation of 0-10% around the value (X±10%). In the context of melting temperatures where the term "about" is used, the melting temperatures are within 0.5° C. of the stated melting temperature.

Having now generally described the invention, the same will be more readily understood by reference to the following examples, which are provided by way of illustration and are not intended as limiting. It is understood that various modifications and changes can be made to the herein disclosed exemplary embodiments without departing from the spirit and scope of the invention.

EXAMPLES

Materials and Methods

Production of *P. berghei* Lysate

GFP transgenic *P. berghei* (ANKA strain) was obtained from the American Type Culture Collection (ATCC, Manassas, Va.). Swiss Webster mice were purchased from Envigo (Indianapolis, Ind.). Mice were infected with *P. berghei* through i.p. injection. The parasitemia was checked every other day using Giemsa staining of thin blood smears. When the parasitemia reached 10%, gametocytes were induced by i.p. injecting mice with 60 mg phenylhydrazine hydrochloride (Santa Cruz Biotechnology, Dallas, Tex.) per kilogram body weight (4 mg/mL, dissolved in PBS). Two days later, *P. berghei*-infected red blood cells and uninfected red blood cells were collected, washed three times with PBS, and re-suspended in PBST (1×PBS containing 0.2% Tween-20). The lysates were prepared by ultra-sonication of cells 6 times with 10 seconds (s) each and 50 s pause on ice, followed by centrifugation at 8,000×g for 5 minutes (m) to remove intact cells and insoluble aggregates. The proteins in supernatants were used for pulldown assay.

Enzyme-Linked Immunosorbent Assay (ELISA) to Determine the Interaction Between Insect Cell-Expressed Recombinant FREP1 and *P. berghei*

High Five insect cell expressed FREP1 and anti-FREP1 polyclonal Ab was obtained. GFP transgenic *P. berghei* (ANKA strain) was obtained from the American Type Culture Collection (ATCC, Manassas, Va.). Swiss Webster mice were purchased from Envigo (Indianapolis, Ind.). The mice were infected with *P. berghei* through i.p. injection. The parasitemia was checked every other day using Giemsa staining of thin blood smears. When the parasitemia reached 10%, gametocytes were induced by i.p. injecting mice with 60 mg phenylhydrazine hydrochloride (Santa Cruz Biotechnology, Dallas, Tex.) per kilogram body weight (4 mg/mL, dissolved in PBS). Two days later, *P. berghei*-infected red blood cells and uninfected red blood cells were collected, washed three times with PBS, and re-suspended in PBST (1×PBS containing 0.2% Tween-20). The lysates were prepared by ultra-sonication of cells 6 times with 10 seconds (s) each and 50 seconds pause on ice, followed by centrifugation at 8,000×g for 5 minutes (m) to remove intact cells and insoluble aggregates. The proteins in supernatants were used for ELISA and pulldown assays. The ELISA method used to study FREP1-parasite interaction has been described in detail by Niu et al. A 96-well plate (Brand, Wertheim, Germany) was coated with 2 mg/mL lysates (measured by Bradford assay) and incubated overnight at 4° C. The next day, each well was incubated with the following solutions: 200 µL blocking buffer (2 mg/mL BSA in PBS) for 1.5 hour (hr), 100 µL recombinant FREP1 protein (100 µg/mL) at room temperature (RT) for 1 hr, 100 µL of purified anti-FREP1 Ab (1:2,000 dilution with PBST) for 1 hr at RT, and 100 µL of alkaline phosphatase-conjugated anti-rabbit IgG (1:20,000 dilution in PBST) for 45 m at RT. The wells were washed with PBST three times between incubations. In the end, the plates were developed with 100 µL of p-NPP solution (Sigma-Aldrich, St. Luis, Mo.) until the colors appeared. Finally, A405 was measured. Each experiment was repeated three times and the t-test was used to compare the difference between the control and the experimental group.

Immobilizing FREP1 onto Magnetic Beads

About 300 µL of N-hydroxysuccinimide (NHS) ester-activated magnetic beads (Thermo Fisher, Weston, Fla.) were placed into a 1.5 mL microcentrifuge tube on a magnetic stand, and the supernatant was discarded after bead adsorption. Beads were then washed with 1 mL of ice-cold 1 mM hydrochloric acid with gentle vortex for 15 s. After discarding the supernatant, 300 µL of purified FREP1 protein (in 50 mM borate, pH 8.5) was added immediately and vortexed for 30 s. The mixture was incubated for 1-2 hr at RT on a rotator. During the first 30 m of the incubation, the tube was vortexed for 15 s every 5 m.

For the remaining time, the tube was vortexed for 15 s every 15 m. FREP1-coupled magnetic beads were then washed twice with 1 mL of 0.1 M glycine (pH 2.0) for 15 s and once with 1 mL of ultrapure water for 15 s. Next, 1 mL of Quenching Buffer (3M ethanolamine, pH 9.0) was added, vortexed for 30 s, and incubated for 2 hr at RT on a rotator. Finally, FREP1-coupled magnetic beads were stored within 300 µL Storage Buffer (50 mM borate with 0.05% sodium azide) at 4° C. The coupling efficiency assessment was performed using Bradford assay measuring the amount of FREP1 proteins in the solution before and after coupling. About 13 µg of FREP1 protein was covalently linked to 1.0 mg beads.

Affinity Chromatography and Quantitative Mass Spectrometry to Identify FBP Proteins

*P. berghei* lysate (e.g., 1 mL) was incubated with FREP1-coupled magnetic beads (e.g., 50 µL) at 4° C. for 2 hr with gentle rotation. The beads were then washed three times to remove non-specifically bound proteins with Pierce IP Lysis Buffer (catalog number: 87787). The retained proteins were eluted with 6 M urea solution. In the control group, procedures were the same as the experimental group, with the exception of the use of glycine-deactivated NHS ester-magnetic beads to replace FREP1-coupled beads. The elusion samples were analyzed with 12% SDS-PAGE. The SDS-PAGE gel was stained with the Coomassie-brilliant blue R250. Specific protein bands on the SDS-PAGE gel were excised and analyzed by quantitative mass-spectrometry (Oklahoma State University Mass Spectrometry Service Center). The raw data is available upon request. The signals were searched against *P. berghei* (ANKA strain) protein database (plasmodb.org) to identify peptide hits. The difference in protein abundance between the control and the experiment group was obtained using a published approach. Briefly, the spectral count data were collected using Multi-dimensional Protein Identification Technology. The Fisher Exact Test is used to calculate the difference p-value using Scaffold (Proteome Software Inc). The calculated p values were transformed to probabilities by an equation of probability equals to $(1-p) \times 100$.

Expression of Active Candidate Proteins Using Baculovirus in Insect Cells to Verify Protein-Protein Interaction Gene-specific DNA oligos (Table 1) were used to clone the identified FBP genes from *P. berghei* by PCR. PCR products were digested with restriction enzymes and ligated into pFastBac1, and positive recombinant plasmids were transformed into DH10Bac competent cells. Depending on primer sequences, PCR products were digested with restriction enzymes Bam H1 and Xba I (New England BioLabs, MA) or Bam HI and Xho I (New England BioLabs, MA). The column isolated DNA fragments were ligated into our modified pFastBac1 plasmid having 6×His tag at C-terminus, and positive recombinant plasmids were transformed into DH10Bac competent cells.

TABLE 1

Primers for FBPs expression using baculovirus system:

| Gene ID | Primer Name | Primer Sequence [SEQ ID NO] |
|---|---|---|
| PBANKA_1365500 | Forward | 5'-CGGGATCCATGAAGAAAGGAAATAACG-3' [20] |
|  | Reverse | 5'-CGCTCGAGCATAGGTTTTGCTCTAC-3' [21] |
| PBANKA_0701600 | Forward | 5'-CGGGATCCATGCCGCAATGGGGGACTGGTA-3' [22] |
|  | Reverse | 5'-GCTCTAGAATCCTTTTGATTCATTGGGT-3' [23] |
| PBANKA_0417700 | Forward | 5'-CGGGATCCATGAGAGAAGTAATAAGTATAC-3' [24] |
|  | Reverse | 5'-GCTCTAGAATAGTCTGCCTCATATCCTTC-3' [25] |
| PBANKA_1316400 | Forward | 5'-CGGGATCCATGGAAGAAATGCGATCATTAC-3' [26] |
|  | Reverse | 5'-GCTCTAGATCGTCGTCTACTGGATCGATTC-3' [27] |
| PBANKA_1309700 | Forward | 5'-CGGGATCCATGAAAGGTTTTAATAATTTTC-3' [28] |
|  | Reverse | 5'-GCTCTAGAGTAATATTTATTTCCGCCTC-3' [29] |
| PBANKA_0711900 | Forward | 5'-CGGGATCCATGGCTAACGCAAAAGCAAAGC-3' [30] |
|  | Reverse | 5'-GCTCTAGAATCAACTTCTTCAACAGTTGGTC-3' [31] |
| PBANKA_0307800 | Forward | 5'-CGGGATCCATGAAAGCTGCTAAAAATGAG-3' [32] |
|  | Reverse | 5'-GCTCTAGATTCATTCTTTTTCACAG-3' [33] |
| PBANKA_1133300 | Forward | 5'-CGGGATCCATGGGAAAAGAAAAAACTCAC-3' [34] |
|  | Reverse | 5'-GCTCTAGATTTTTTTGCTGGTGCTTTAGC-3' [35] |
| PBANKA_1234500 | Forward | 5'-CGGAATTCATGGCAAAAATTACAAAAATCG-3' [36] |
|  | Reverse | 5'-GCTCTAGATTCACCCATTTTATTAAATCCTTC-3' [37] |

Note:
Underlined sequences are restriction

Recombinant bacmids were extracted from white colonies. Following the manufacturer's manual, 0.5 mL 2×105/mL sf9 cells in complete medium (Grace's medium (ThermoFisher) containing 10% FBS) were deposited into one well of a 24-well plate. After incubation for 30 m, the supernatant was removed. Meantime, one µL bacmid DNA (1 µg/µL) combined with 25 µL Grace's medium was mixed gently, and 2 µL Cellfectin II (ThermoFisher) diluted with 25 µL Grace's medium was mixed gently. The DNA mixture and Cellfectin II mixture were combined and incubated for 30 m at RT, and then added to the above prepared sf9 cells.

After incubation for 5 hr at 27° C., the transfection mixture was removed and 0.5 mL complete growth medium (Grace's medium with 10% FBS and 1× Penicillin/Streptomycin) was added. After incubation at 27° C. for three days, the medium containing recombinant baculovirus particles was collected and used to infect High Five insect cells to express recombinant proteins. The expressed proteins were confirmed with ELISA by detecting the His-tag at the C-terminus of recombinant proteins, after three passages (10 µl old cell culture to 200 µl new cell culture).

Determination of FBPs-FREP1 Interaction by ELISA

Three passages later, protein expression was confirmed with ELISA through detecting the 6×His tag at the protein C-terminus. The ELISA method is similar as the previously described. Briefly, the expression levels of different FBPs in the cell lysate were normalized to 1 nM and then a 96-well plate was coated overnight with 100 µl cell 298 lysate to detect interactions with FREP1. After blocking the plate with 100 µl 0.2% BSA in 1×PBS, 100 µl recombinant FREP1 in PBS (1 nM) was introduced onto the wells and incubated for 1.5 h with the plate at RT. Purified anti-FREP1 Ab (3 µg/mL in PBS) was used to detect any retained FREP1. Followed by 100 µl 2nd Ab (1:10,000 dilution in PBS). The plates were developed with 100 µL of p-NPP solution (Sigma-Aldrich, St. Luis, Mo.) until the colors appeared. The absorbance at 405 nm was measured using a plate reader. Between each incubation, wells were washed with 100 µL PBST three times with 3 m incubation each time. For the control group, 1 nM of CAT protein (Chloramphenicol acetyltransferase, containing a 6×His tag at C-terminus) expressed in the same baculovirus-expression system (Thermo Fisher) was used to coat plate wells. The P. berghei-infected blood cell lysate (1 mg/ml proteins) was used to coat wells as the positive control. Each sample was repeated in three wells and the t-test analysis was used to determine the difference between the negative control and experimental group.

Production of Ab Against FBPs

To generate sufficient amount of proteins for immunization, the coding sequence (CDS) of P. falciparum HSP70 was amplified with primers of 5'-CGGGATCCATGGCTAACGCAAAAGCAAAGC-3' (SEQ ID NO: 38) and 5'-CGCAAGCTTTTAATCAACTTCTTCAACAGTTGGTC-3' (SEQ ID NO: 39). The CDS of P. falciparum α-tubulin 1 was amplified with primers of 5'-CGGGATCCATGAGAGAAGTAATAAGTATAC-3' (SEQ ID NO: 40) and 5'-GCTCTAGAATAGTCTGCCTCATATCCTTC-3' (SEQ ID NO: 41). The sequences underlined are restrict enzyme recognition sites. The DNA fragments were digested with corresponding restriction enzymes and ligated into the pQE30 plasmid. Recombinant proteins were expressed in Escherichia coli M15 strain induced by 1 mM isopropyl 1-thio-β-D-galactopyranoside (IPTG). After 3-4 hr induction at 37° C., cells were lysed in buffer B (8 M urea, 100 mM NaH2PO4, 10 mM Tris-Cl, pH 8.0). Recombinant FBPs were purified on Ni-NTA column using the manufacturer's protocol (QIAGEN). Customized polyclonal Ab was generated in Swiss Webster mice by priming with 20 µg purified recombinant FBPs in CFA adjuvant 322 (v/v, 1:1), followed by two additional boosts (with 2-weeks intervals) with 20 µg proteins in IFA adjuvant (v/v, 1:1). An identical volume of buffer B with the same adjuvant was used as a negative control to immunize mice. Fifty days later, mouse sera were collected. Ab titers were checked using ELISA with a serial dilution of the collected sera added into the 96-well plates that had already been coated with the corresponding antigens.

Equivalent amounts of control mouse serum were used as negative controls. The cut-off criterion was the dilution that OD405 signal decreases to the mean of negative control replicates plus 2×S.D.

Culture *P. falciparum*

*P. falciparum* parasites (NF54 strain from MR4, Manassas, Va.) were maintained in 5 mL RPMI 1640 medium (Life Technologies) supplemented with 10% heat-inactivated (56° C. for 45 min) human AB+ serum (Interstate Blood Bank, Memphis, Tenn.), 12.5 g/ml hypoxanthine, and 4% hematocrit using a 6-well cell culture plate (Corning, N.Y.) in a candle jar at 37° C. The parasitemia or gametocytemia was analyzed every day by Giemsa staining of thin blood smears. When the parasitemia reaches 5%, 0.5 ml of culture was transferred into 5 ml fresh complete RPMI-1640 supplemented with 4% hematocrit. The remailing culture was maintained for another 10 days to two weeks before using it to infect mosquitoes.

To prepare ookinetes, *P. falciparum* cultures harboring 2-5% stage V gametocytes were diluted 10-fold in complete RPMI 1640 supplemented with 20% head-inactivated human AB+serum and 50 µg/mL hypoxanthine and incubated at room temperature for 18-24 h.

Determine the Localization of α-Tubulin-I on Live *P. falciparum* Ookinete Surface by IFA Rabbit polyclonal Ab against human α-tubulin (ProteinTech, IL, USA) was labelled with CF™ 568 dye (Mix-n-Stain™ CF® Dye Antibody Labeling Kits—CF®568, Biotium Inc, CA). The cultured *P. falciparum* ookinete cell mixtures ($10^5$ cells) were suspended 200 µL incomplete RPMI-1640 medium and were careful deposited on the top of 0.6 mL 65% percoll (100% percoll diluted with incomplete RPMI-1640) in a 1.5 mL plastic tube. After centrifugation at 2,000 rpm for 5 m, the cells at the interface of medium and 65% percoll were collected and 10-fold diluted with incomplete RPMI-1640 medium, and then collected by centrifugation at 2,000 rpm for 5 m. The cells were washed twice with 0.5 mL PBS through centrifugation (2,000 rpm for 5 m). Because the fluorescence is sensitive to light, the following steps were done in dark room. The cells were suspended in 50 µL PBS, and incubated with fluorescence-conjugated anti-α-tubulin Ab (200-fold dilution, final Ab concentration was about 1 µg/mL) for 45 m. The cells were collected and washed with 0.5 mL PBS twice by centrifugation (2,000 rpm for 5 m). Finally, the cells (about $10^4$ cells) were suspended in 20 µL PBS, and 4 µL were deposited onto a slide coverslip. Immediately after dry, the cells on a coverslip were mounted on a slide with 5 µL of Vectashield mounting media (Vector Laboratories, Burlingame, Calif.). After incubated at 4° C. for 2 h, the cells were examined using a Nikon Eclipse Ti-S fluorescence microscope. The cells treated the same as the above except using unrelated antibodies (anti-His) were used as a negative control. Cells on slides were fixed with methanol and incubated with fluorescence-conjugated anti-α-tubulin Ab (200-fold dilution, final Ab concentration was about 1 µg/mL) as a positive control.

Ab Transmission-Blocking Assays of *P. falciparum* Infection in *An. Gambiae*

Standard membrane feeding assays (SMFA) were performed as previously reported by Zhang et al. (2015) and Niu et al. (2015). Antibody or anti-serum were mixed with cultured *P. falciparum* and fed 3-5-day-old female *An. gambiae* mosquitoes. After feeding, the engorged mosquitoes were maintained with 8% sugar (w/v) at 27° C. Seven days after infection, mosquitoes were dissected, and the midguts were stained with 0.2% mercurochrome for 30 min. Then, the number of oocysts was counted under light microscopy. Nonparametric statistical analysis, e.g. Mann-Whitney-Wilcoxon test that was implemented in GraphPad Prism software (Version 6h, San Diego, Calif.) was used to analyze the inhibition effect of Ab.

To rule out the effect of other components in sera, the purified rabbit polyclonal Ab (Abeam, Cambridge, Mass.) was used in malaria transmission-blocking assay. About 6 µL rabbit polyclonal Ab against human α-tubulin (0.3 mg/mL) was added into 200 µL *P. falciparum*-infectious blood (final Ab concentration was about 0.01 mg/mL) and fed to *An. gambiae*. The same amount of non-related purified rabbit polyclonal Ab (anti-V5 tag) was used as a control. Seven days late, the number of oocysts in mosquito midguts was counted for statistical analysis by Wilcoxon test.

The Ookinete Conversion Assays in the Presence of Ab

First, the number of gametocytes in cultures was counted under microscope using the blood smear. About 1 mL 15-day *P. falciparum*-cultured blood that harbors stage V gametocytes was collected by centrifugation (800×g for 4 m) and resuspended into 10-fold ookinete cultures (complete RPMI-1640 without $NaHCO_3$). About 3 µL of polyclonal anti-human α-tubulin Ab (0.3 mg/mL, Abcam) was then added into 150 µL *P. falciparum*-infectious blood (final Ab concentration was about 6 µg/mL) to a well in a 96 well plate. Then the parasites were incubated under 21-23° C. for about 16 hours. The same amount of nonrelated purified rabbit Ab (anti-V5) was used as a control. The number of 413 ookinetes was counted, and the ookinete conversion rate (CR), the percentage of ookinetes among the total *P. falciparum* gametocytes, was calculated.

In view of the many possible embodiments to which the principles of the disclosed invention may be applied, it should be recognized that the illustrated embodiments are only examples and should not be taken as limiting the scope of the invention.

Unless defined otherwise, all technical and scientific terms herein have the same meaning as commonly understood by one of ordinary skill in the art to which this invention belongs. Although any methods and materials, similar or equivalent to those described herein, can be used in the practice or testing of the present invention, the preferred methods and materials are described herein.

All patents, patent applications, provisional applications, and publications referred to or cited herein are incorporated by reference in their entirety, including all figures and tables, to the extent they are not inconsistent with the explicit teachings of this specification.

Following are examples which illustrate procedures for practicing the invention. These examples should not be construed as limiting. All percentages are by weight and all solvent mixture proportions are by volume unless otherwise noted.

Example 1—FREP1 Binds to *P. berghei* Parasites

Figure 1B:
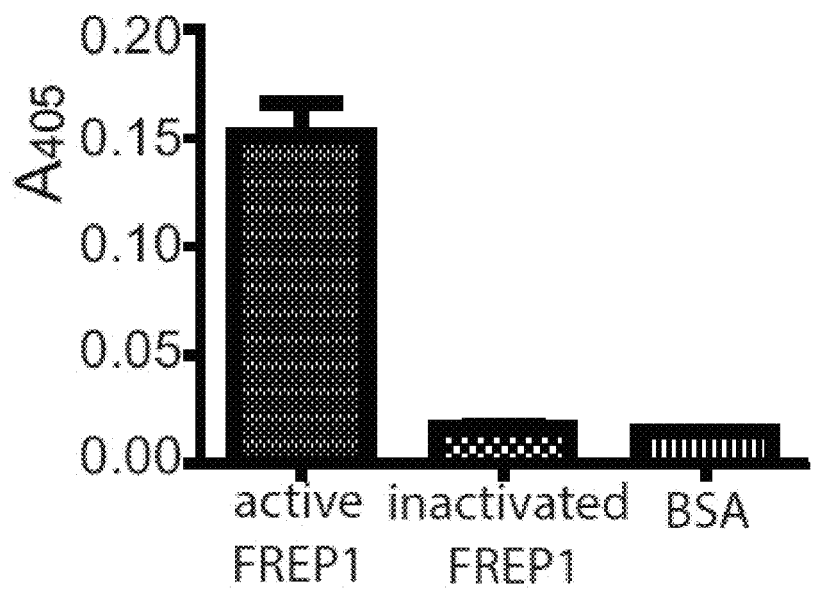

Anti-FREP1 antibodies prevented *P. berghei* from infecting *An. gambiae*. FREP1 was able to bind to *P. falciparum*. Here, the interaction between FREP1 and *P. berghei* was determined. FREP1 protein was expressed in High Five insect cells and was purified using Ni-NTA column. *P.* berghei-infected mouse blood cell lysate was used to coat enzyme-linked immunosorbent assay (ELISA) plates for ELISA assays, followed by incubation with FREP1, anti-FREP1 Ab, and 2nd Ab sequentially. Uninfected mouse blood cell lysate was used as a control. Results showed that the absorbance at 405 nm (A405) from active FREP1 binding to infected mouse blood lysate was significantly higher than that in the negative control ($p<0.01$) (FIG. 1A). BSA and heat inactivated FREP1 were used to substitute the active recombinant FREP1 in ELISA. The inactivation of recombinant FREP1 protein by heat removed binding signals (FIG. 1B), which confirmed that active FREP1 protein binds to *P. berghei*.

Example 2—Separation of FBPS from *P. berghei*

Figures 2A, 2B, 2C:
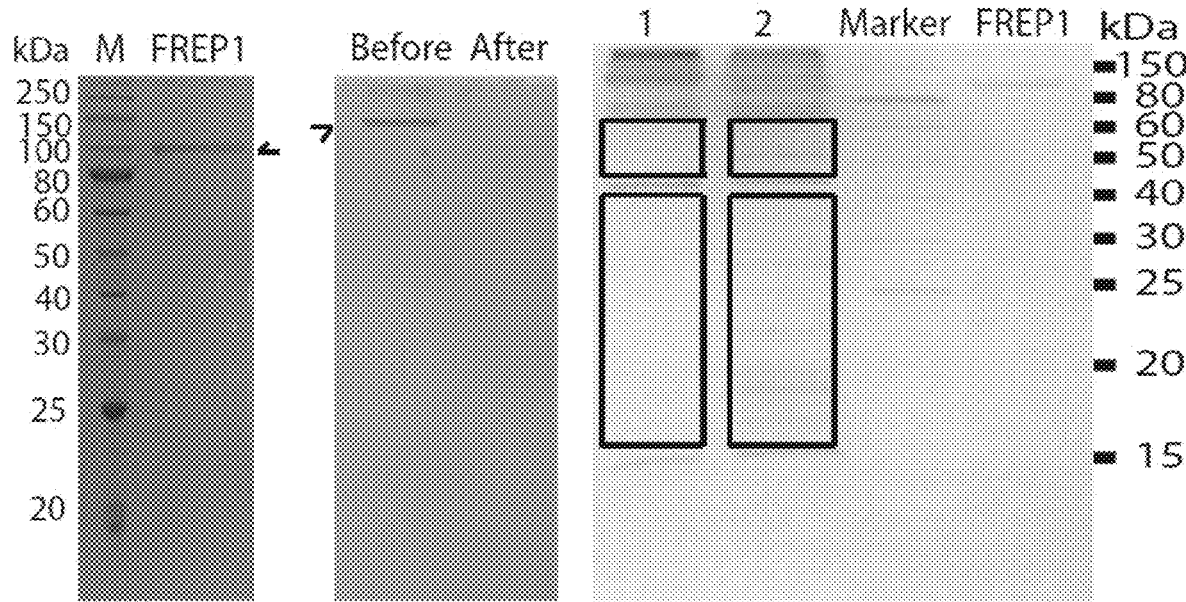
FIGS. 2A-2D identify FBPs from P. berghei. 2A) The insect cell-expressed FREP1 protein was purified by Ni-NTA column. M: Protein molecular marker. The proteins were resolved on 12% SDS-PAGE following by Coomassie Brilliant Blue R-250. 2B) FREP1 was immobilized covalently onto the magnetic support. "Before" and "After" columns on 12% SDS-PAGE represent the FREP1 supernatant before coupling and after coupling with magnetic beads, respectively. 2C) Pull-down of P. berghei-infected cell lysate using FREP1-linked magnetic beads. The proteins were resolved on 12% SDS-PAGE following by silver staining. Lanes: 1, Pull-down of P. berghei-infected cell lysate by beads without FREP1 conjugation (negative control); 2, Pull-down of P. berghei-infected cell lysate with FREP1-conjugated magnetic beads; Marker, Protein markers; FREP1, purified FREP1 protein used to locate the recombinant FREP1 in lane 2. The rectangle highlights specific protein bands in the experimental group. This area was excised and analyzed by mass spectrometry. 2D) Determination of the interaction between recombinant FBPs proteins and FREP1 protein by ELISA assays. The same amount of FBP1, FBP2, FBP3, FBP4, FBP5, FBP6, FBP7, FBP8, FBP9 recombinant proteins were used to coat ELISA wells. N: Negative control coated with insect cell-expressed CAT protein. P: positive control coated with P. berghei infected blood cell lysate. Each sample was conducted in three wells in one plate and the same experiment was conducted three times.

FBPs were isolated using FREP1-linked affinity chromatography. The insect cell-expressed recombinant FREP1 protein was purified by using a Ni-NTA column, and the purity of FREP1 was estimated to ~99% (FIG. 2A). The purified FREP1 protein was covalently coupled to magnetic beads through N-hydroxysuccinimide (NHS) ester-activated chemical groups. After coupling reaction, no detectable FREP1 was eluded from the magnetic beads (FIG. 2B). About 13 jig of FREP1 proteins were bound to 1.0 mg beads. *P. berghei*-infected mouse blood lysate was incubated with the FREP1-bound magnetic beads to obtain FBP proteins. Magnetic beads without covalently bound FREP1, but deactivated with glycine, were used as a negative control. After washing, the bound proteins and FREP1 were eluded with reducing SDS-PAGE loading buffer and loaded onto SDS-PAGE. Multiple proteins including FREP1 were recovered from the experimental pull-downs (FIG. 2C), suggesting that FREP1 directly or indirectly bound to several proteins.

To identify these proteins, gel bands were excised from both experimental and control lanes and analyzed by quantitative mass spectrometry. Mass-to-charge ratio of the ions was searched against the *P. berghei* (ANKA strain) protein database (https://plasmodb.org/plasmo/). Nine *Plasmodium* proteins were identified with >99.80% identification probability that were present in the experimental samples but not in the control samples (Table 2).

TABLE 2

Candidate FBP proteins from *P. berghei* through pull-down assays.

| FBP Index | Accession # (PBANKA_) | Gene Name | MW (kDa) | Identification probability | Signal peptide |
|---|---|---|---|---|---|
| 1 | 0711900 | Hsp70 | 75 | 100.00% | No |
| 2 | 1309700 | RNA helicase DDX5 | 59 | 100.00% | No |
| 3 | 0417700 | A-tubulin-I | 50 | 100.00% | No |
| 4 | 1133300 | EF-1 α | 49 | 100.00% | No |
| 5 | 1316400 | U1 snRNA associated protein | 38 | 100.00% | No |
| 6 | 1365500 | Exported protein IBIS 1 | 37 | 100.00% | No |
| 7 | 0307800 | Unknown | 32 | 100.00% | No |
| 8 | 0701600 | Unknown | 26 | 100.00% | No |
| 9 | 1234500 | Unknown | 23 | 99.80% | No |

To confirm interactions between FREP1 and the putative FBPs, the coding sequences (CDS) of the nine FBP candidates were amplified by PCR from *P. berghei*, inserted into baculovirus, and expressed in High Five insect cells. The expressed recombinant proteins were used to determine their specific interaction with FREP1 by using ELISA as described in methods. The same amount of recombinant FBPs (1 nM) in phosphate buffered saline (PBS) was used to coat the ELISA plates respectively, followed by incubation with same amount of insect cell-expressed recombinant FREP1 (1 nM). The bound FREP1 was detected using purified anti-FREP1 Ab (3 μg/mL).

For the control group, the same amount of acetyltransferase (CAT) protein expressed in the same system as FBPs was used to coat plate wells as the negative control. *P. berghei*-infected blood cell lysates (1 mg/ml protein) was used to coat ELISA wells as the positive control. Each sample was conducted in three wells in one plate and the same experiment was conducted three times. Results showed that six of nine FBP candidates, e.g., FBP1, FBP3, FBP5, FBP6, FBP8, and FBP9 retained significantly more amount of FREP1 than that of the negative control ($p<0.01$) (FIG. 2D), suggesting FREP1 bound to broad spectrum of proteins. On the other hand, FBP2, FBP4, and FBP7 did not. Therefore, FBP1, FBP3, FBP5, FBP6, FBP8, and FBP9 were able to bind to FREP1 protein in vitro. Among the binding proteins, FBP3 exhibited the strongest signal, suggesting the highest affinity between FREP1 and FBP3. Notably, FBP3 is *Plasmodium* α-tubulin-I.

Figure 2D:
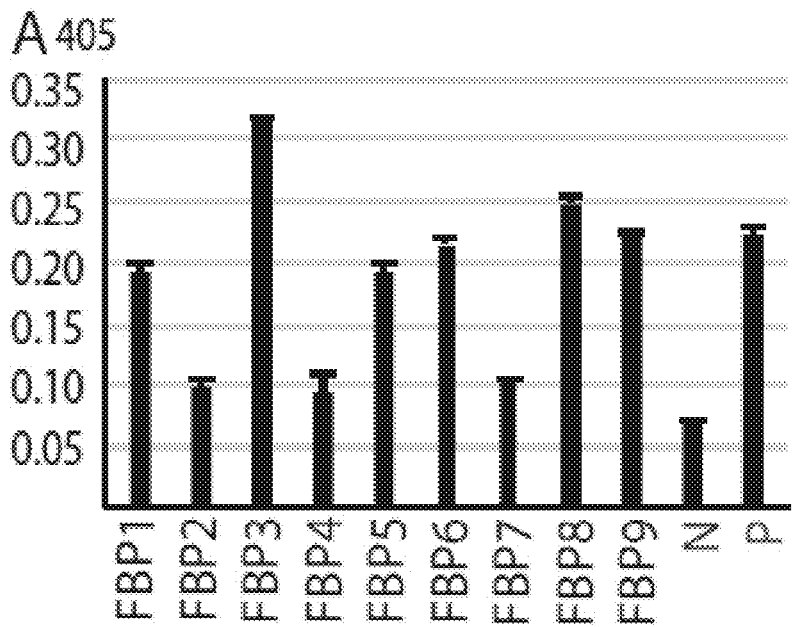

Example 3—Anti-α-Tubulin Polyclonal Ab Binds to the *P. falciparum* Ookinete Apical Complex The localization of α-tubulin-I on ookinetes was examined and its accessibility in non-permeabilized, live ookinetes was tested. To do this, we used α-tubulin-I-specific antibodies instead of FREP1 as a probe, given our findings that FREP1 potentially binds to a broad-spectrum of proteins (FIG. 2D).

Figure 3A:
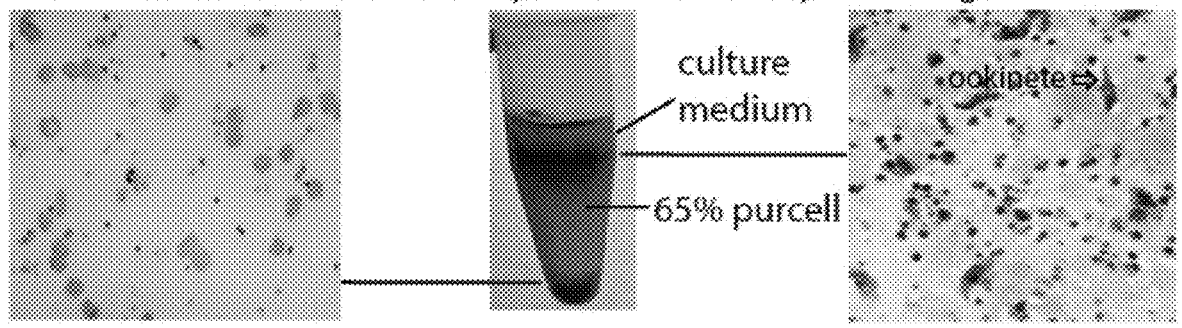
FIGS. 3A-3C show immunofluorescence assay showing that anti-α-tubulin Ab bound to the living P. falciparum ookinetes at their apical end. 3A) Enriching ookinetes through differential density centrifugation using 65% percoll. 3B) IFA assays localized α-tubulin-I on living ookinetes. The co-localization of P. falciparum (nuclei, blue color) and α-tubulin-I (red). Closeup of individual ookinetes showed that Ab bound to apical end of living *P. falciparum* ookinetes. Closeup of apical complex showed that anti-α-tubulin Ab likely bound to the apical ring of living ookinetes. 3C) Ookinetes stained with CF568 dye conjugated anti-His antibodies as a negative control showed no binding. Methanol fixed ookinetes stained with anti-α-tubulin Ab, showing that Ab could stain α-tubulin-I tubulin inside cells.

Polyclonal Ab against α-tubulin-I was labelled with CF™ 568 dye and the interaction between Ab and living ookinetes was investigated. *P. falciparum* ookinetes were cultured in vitro and enriched by differential density centrifugation using 65% percoll. Uninfected red blood cells and cell debris sedimented to the bottom of the percoll, while gametocytes and ookinetes were enriched at the interface of percoll and the culture medium (FIG. 3A). The enriched gametocytes and ookinetes were washed and incubated with the CF™ 568-conjugated anti-α-tubulin Ab. After removal of the unbound Ab, the cells were deposited onto coverslips and counterstained with DAPI.

Figure 3B:
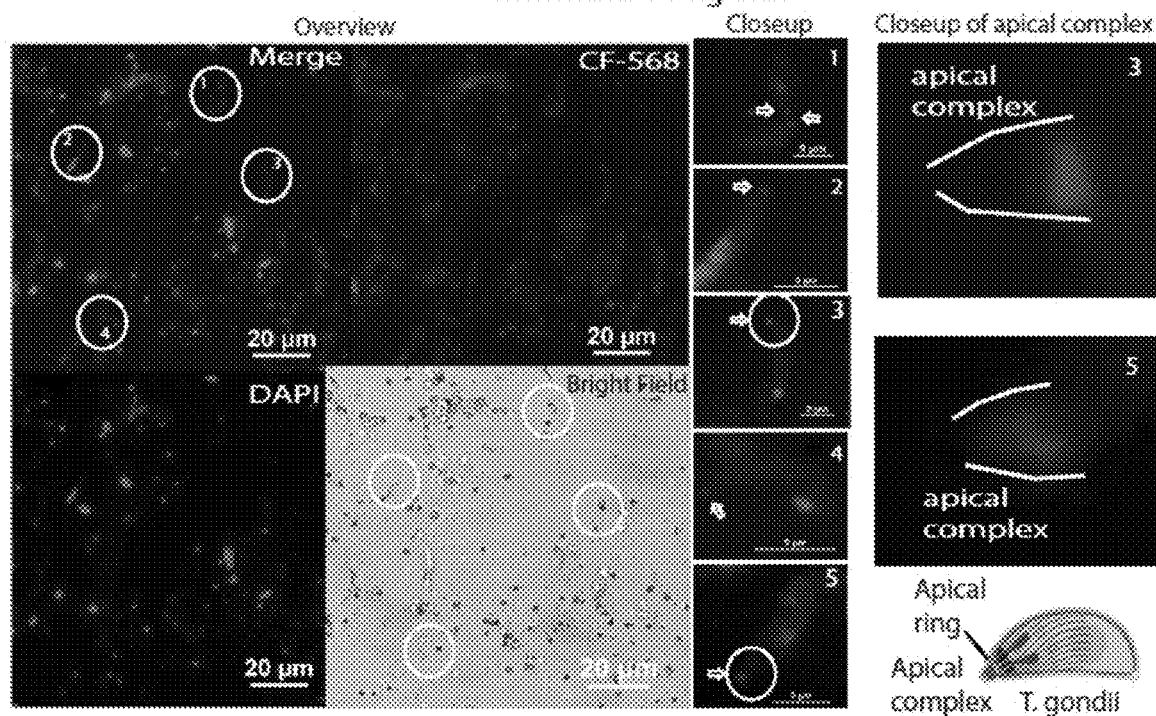

Fluorescence microscopy revealed than anti-α-tubulin Ab bound to the apical end of ookinetes, as shown in FIG. 3B. The Ab bound to cells shown in red due to the conjugated-CF-568. The nuclei of ookinetes and gametocyte were stained by DAPI staining. The DAPI also stained many free parasites and asexual stage parasites. High-powered examination of individual ookinetes revealed that intense signal localized to apical ends (pointed by white arrows in FIG. 3B, closeup), supporting anti-α-tubulin Ab recognized the α-tubulin-1 of the living ookinetes at their apical ends. Notably, anti-α-tubulin-1 staining was not concentrated at the very distal tip of the ookinetes (FIG. 3B, closeup of apical complex), but instead signal was localized to the position of apical rings, further supporting Ab recognized α-tubulin-1 at apical rings of living ookinetes.

Figure 3C:
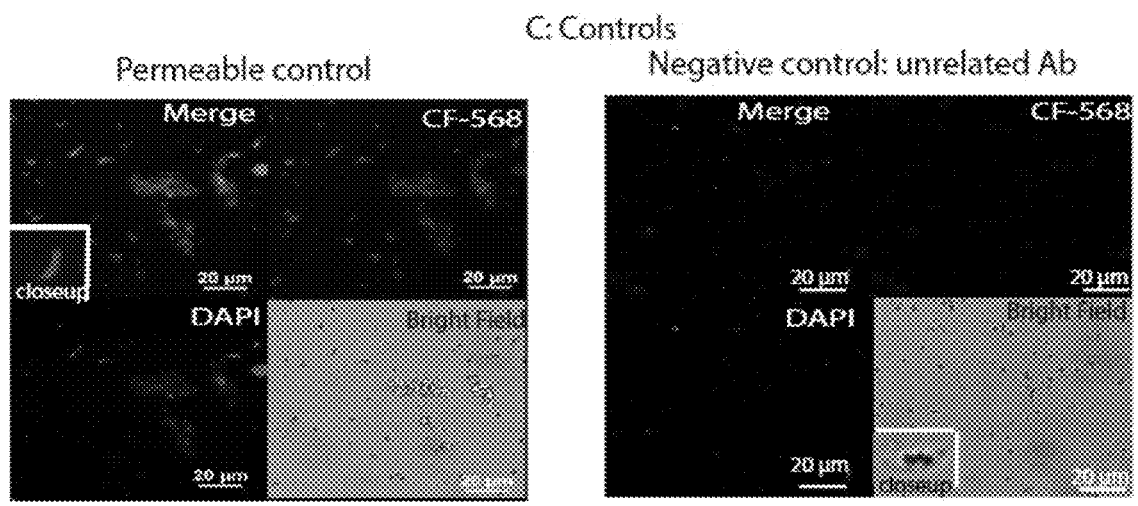

Importantly, fixation with methanol and permeabilization of ookinetes revealed signal that was distributed across the cells (FIG. 3C, permeable control). Substitution of anti-α-tubulin polyclonal Ab with an irrelevant (anti-V5) polyclonal Ab revealed no signal (FIG. 3C, Negative control).

Together, these data support that α-tubulin-I is exposed on the living ookinete surface at apical polar rings.

Figure 4A:
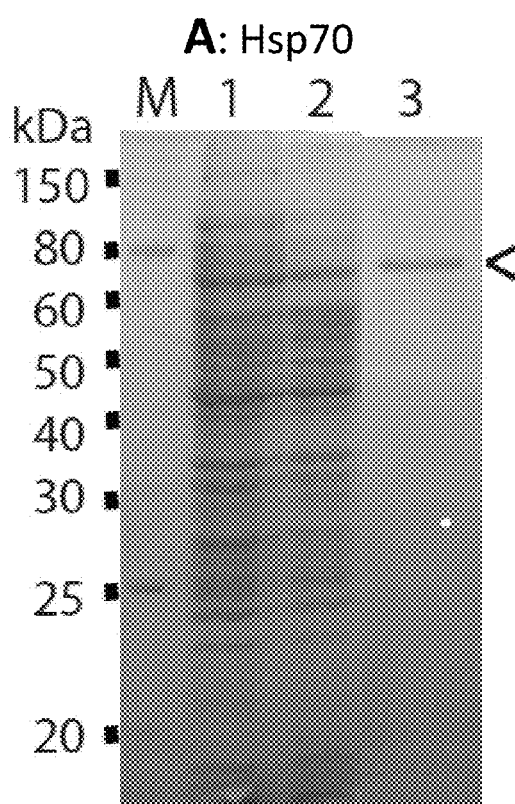
FIGS. 4A-4F show anti-serum against *P. falciparum* α-tubulin-I and Hsp70, and *P. falciparum* transmission-blocking assays by anti-sera. 4A) Expression and purification of *P. falciparum* Hsp70 in *E. coli*. 4B) Expression and purification of *P. falciparum* α-tubulin 1 in *E. coli*. Lanes, M: protein marker; 1: Proteins expressed after induction by IPTG; 2: Proteins before induction; 3: Purified *E. coli* expressed Hsp70 or α-tubulin 1 by using Ni-NTA column, which were analyzed in a separated SDS-PAGE. 4C, 4D) Anti-Hsp70 and anti-α-tubulin 1 Ab were raised in mice respectively with two boosts. The Ab endpoint titers were measured with ELISA. X-axis coordinates show dilutions of antiserum. 4E) Anti-Hsp70 mouse serum did not significantly inhibit *P. falciparum* transmission to mosquitoes (p=0.2). Each dot represents one mosquito. Control is the serum from the mice that immunized with adjuvant only, all other procedures were the same. 4F) Mouse serum against α-tubulin 1 inhibited *P. falciparum* transmission to mosquitoes significantly (p=0.0004). Control is the serum from the mice that immunized with adjuvant only. The experiment was repeated twice, and the results were reproducible.
Figure 4B:
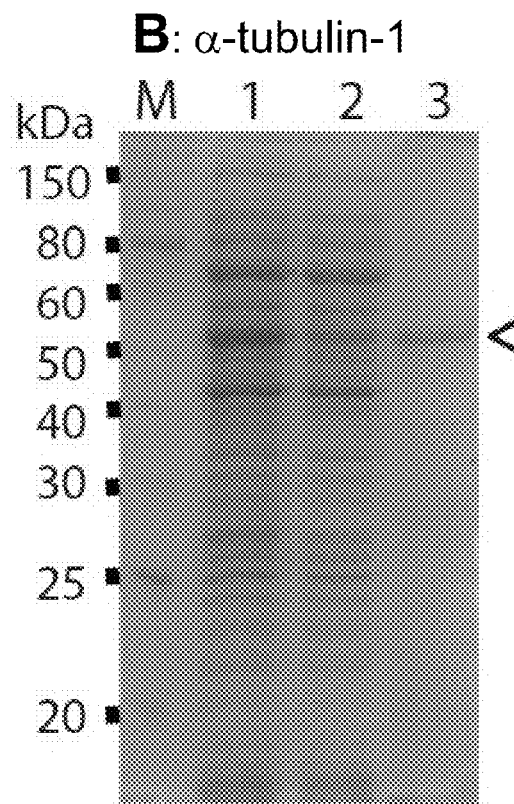
Figure 4C:
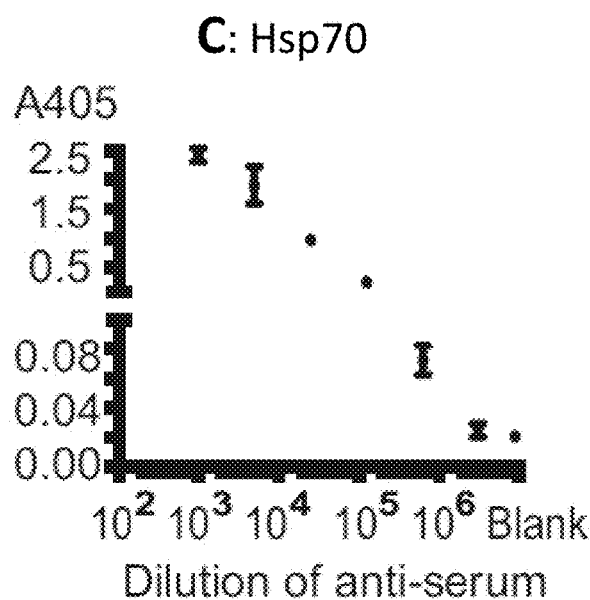
Figure 4D:
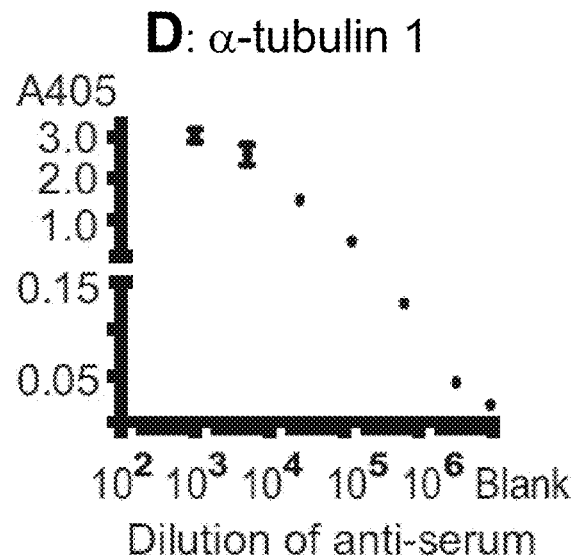
Figure 4E:
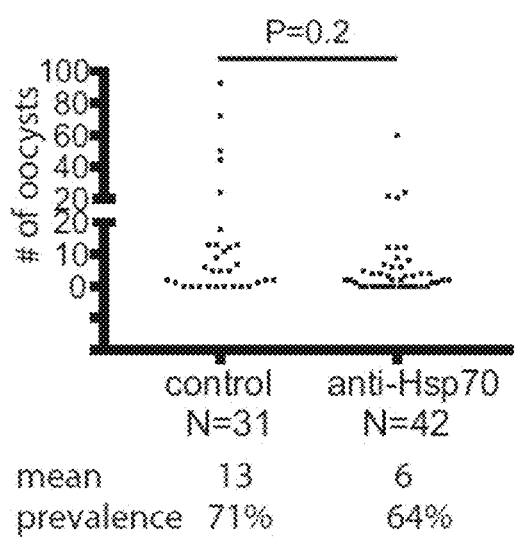
Figure 4F:
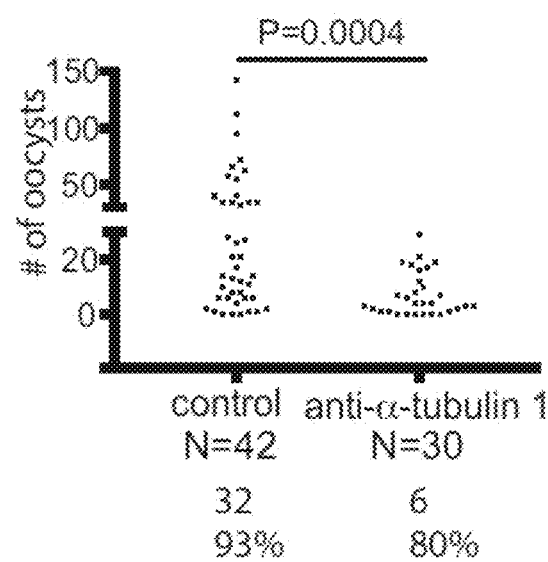

Example 4—Determination of the Effects of Candidate FBPS on Malaria Transmission Using Ab Blocking Assays and Functional Contribution of α-Tubulin-I to *Plasmodium* Infection of Mosquitoes The FREP1-mediated 122 *Plasmodium* invasion pathway is conserved across multiple *Plasmodium* species including *P. falciparum, P. vivax*, and *P. berghei*. Therefore, an FBP related to malaria transmission should be conserved across the three *Plasmodium* species. Given that the interaction signals from *Plasmodium* α-tubulin-I and FREP1 were the highest and the imaging studies support that α-tubulin-I may be exposed in live ookinetes at the apical rings, the membrane feeding assays were next conducted to test whether anti-α-tubulin-I Ab could block *Plasmodium* transmission to mosquitoes. The sequences of the six FBPs among *Plasmodium* species were examined. The results showed that FBP1 (Hsp70) and FBP3 (μ-tubulin 1) were highly conserved (Table 3) with >95% identity across *Plasmodium* species, and the conservation of other four FBP candidates was much less with <83% identity. Hsp70 and μ-tubulin 1 were chosen for further analysis about their effects on malaria transmission.

number of oocysts in each mosquito midgut was examined. Results show that Ab against α-tubulin 1 significantly ($p<0.0004$) reduced the number of *P. falciparum* oocysts in mosquitoes compared to the control (FIG. 4F), while no inhibition was detected for anti-Hsp70 (FIG. 4E). Of note, antiserum against the remaining four FBPs proteins did not show significant inhibition on *P. falciparum* transmission to *An. gambiae* ($p>0.2$).

Figure 5B:
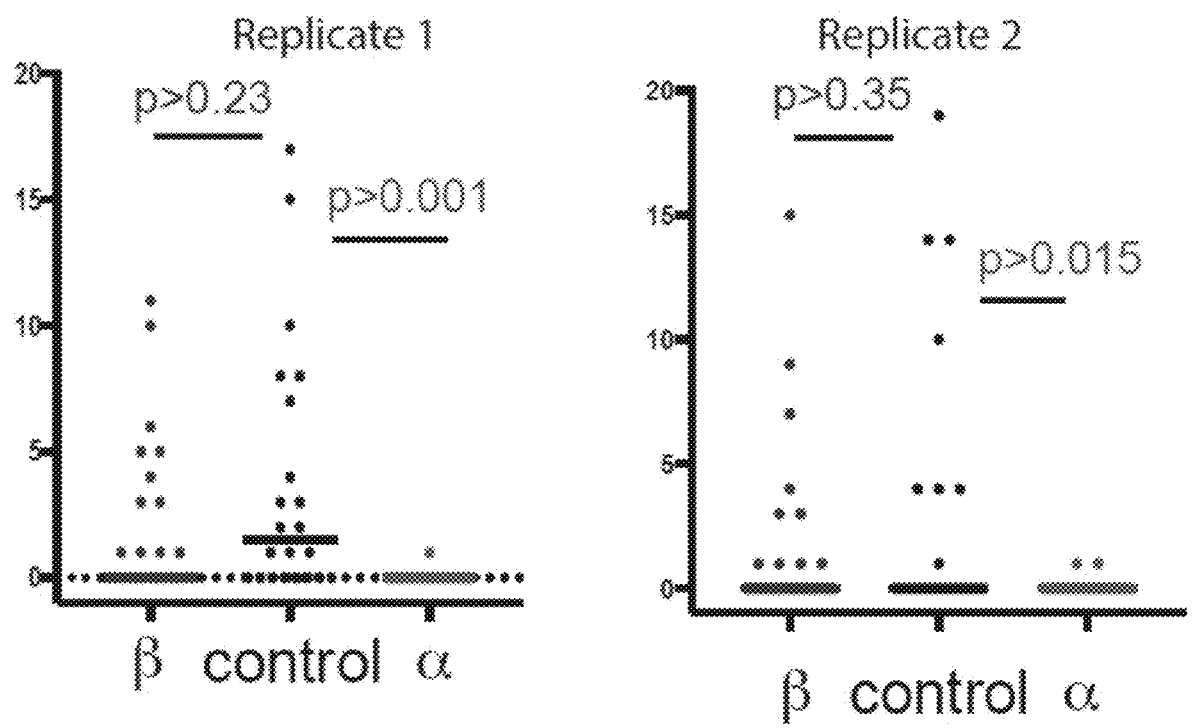
Figure 6:
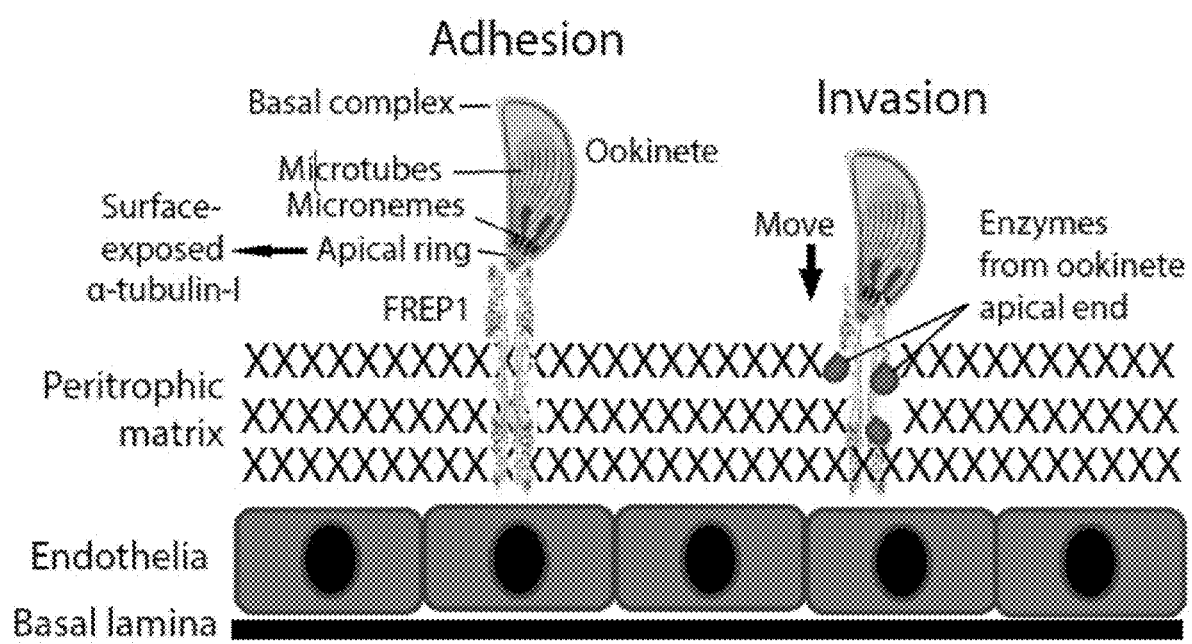
FIG. 6 shows a hypothetical model of FREP1-α-tubulin 1 interaction that mediates the *Plasmodium* transmission to *Anopheles*. The interaction between FREP1 in mosquito midgut peritrophic matrix and α-tubulin-I exposed cells surface at ookinete apical ends directs invasive apparatus opening toward PM, and enzymes released from the parasitic apical opening disrupt midgut integrity. Together, these actions facilitate an ookinete to penetrate the midgut physical barrier for invasion.
Figure 8:
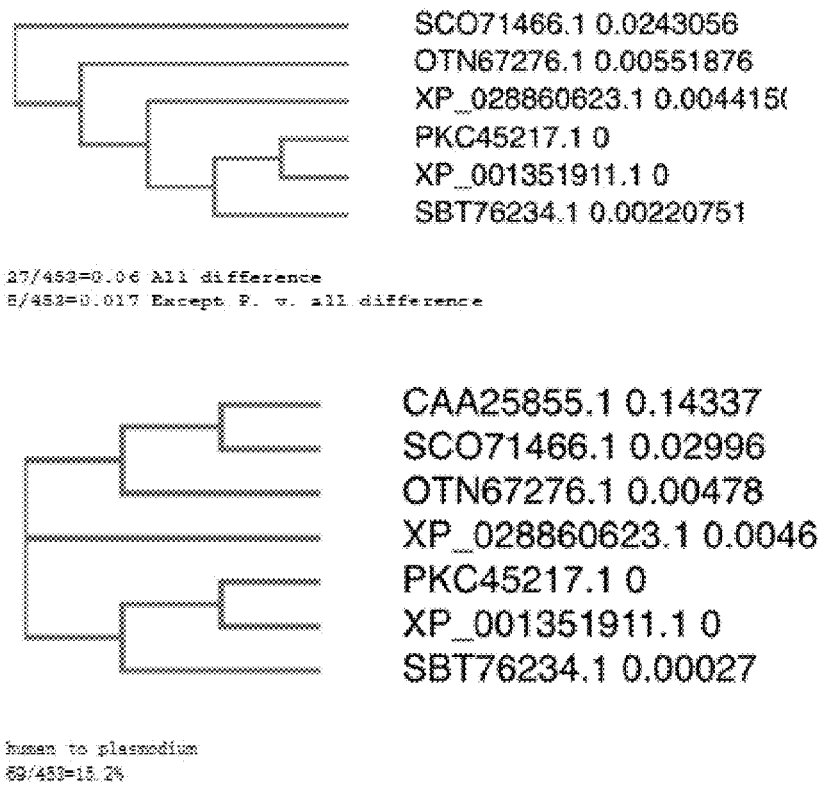
FIG. 8 shows the relationship between various α-Tubulin homologs.

To exclude the possibility that other components of the polyclonal serum were inhibiting mosquito invasion, the transmission-blocking assays were repeated using purified polyclonal Ab. The capacity of purified Ab against human α-tubulin to block *P. falciparum* transmission to mosquitoes was also tested using membrane feeding assays, because *P. falciparum* α-tubulin-I and human α-tubulin sequences are homologous, sharing >84% of identical amino acids (FIG. 5A). The purified Ab was mixed with *P. falciparum*-infected blood and fed to *An. gambiae* and the number of oocysts in mosquito midguts were counted. An irrelevant rabbit polyclonal Ab (anti-V5 tag) was used as a negative control. Ab against human α-tubulin significantly reduced the number of *P. falciparum* oocysts in *An. gambiae* midguts ($p<0.015$), compared to the control serum (FIG. 5B). Strikingly, the infection prevalence rate was decreased from 27% and 68% to 6% and 4%, respectively, in two replicates and oocysts were detectable in only one or two mosquitoes from the anti-α-tubulin experimental feeding groups.

TABLE 3

The coverage and identity of FBP orthologs among *P. berghei*, *P. falciparum* and *P. vivax*.

| | | | Ortholog in *P. falciparum* | | | Ortholog in *P. vivax* | | |
|---|---|---|---|---|---|---|---|---|
| Index (FBP) | Gene in *P. berghei* (# of AA) | Common Name | Accession # (# of AA) | Coverage | Identity | Accession # (# of AA) | Coverage | Identity |
| 1 | PBANKA_0711900 (694) | Hsp70 | 1408240A (681) | 99% | 95% | XP_001614972.1 (680) | 99% | 96% |
| 3 | PBANKA_0417700 (453) | α-tubulin-I | PKC45217.1 (453) | 100% | 98% | SCO71791.1 (453) | 100% | 98% |
| 5 | PBANKA_1316400 (318) | U1 snRNA associated protein | XP_001348676.2 (379) | 91% | 68% | SGX79200.1 (402) | 86% | 71% |
| 6 | PBANKA 1365500 (327) | IBIS 1 | None | | | None | | |
| 8 | PBANKA_0701600 (216) | Not available | XP_002808885.1 (216) | 100% | 78% | XP_001614872.1 (216) | 100% | 83% |
| 9 | PBANKA_1234500 (191) | Not avalable | XP_002808702.1 (192) | 98% | 67% | SCO73154.1 (191) | 90% | 67% |

Note:
"# of AA" stands for the number of amino acids in a protein.
Accession numbers of *P. berghei* genes begins with PBANKA_, which is from PlasmoDB.
Coverage: the percentage of *P. falciparum* or *P. vivax* orthologs were aligned by the *P. berghei* ortholog.

Similar to cytoskeleton proteins, Hsp70 is highly abundant in cells. Ab blocking assays were used to examine the effects of Hsp70 and α-tubulin 1 on *P. falciparum* transmission to *An. gambiae*. To produce sufficient proteins, Hsp70 and α-tubulin-1 were PCR-cloned from *P. falciparum*, expressed them in *E. coli*, and purified them with Ni-NTA columns (FIGS. 4A, and B). The purified proteins (FIGS. 4A and B, lane 3) were used to immunize mice. After two boosts, antisera were collected. Ab titers for Hsp70 and α-tubulin 1 determined by ELISA were approximately $3\times10^6$ (FIGS. 4C and D). Ten percent of antiserum mixed with cultured *P. falciparum* was used to infect *An. gambiae*. Ten percent of the serum from the control mice, which were immunized with adjuvant only, mixed to infect mosquitoes as a control. Engorged mosquitoes were maintained and the Since *P. falciparum* α-tubulin-I and α-tubulin normally form heterodimers and they are different with 42.6% identical sequences, the capacity of Ab targeting α-tubulin to block transmission was also investigated in the membrane feeding assays. Similar to α-tubulin, *P. falciparum* α-tubulin and human α-tubulin share 85.5% identical amino acid sequences. However, there was no significant difference of oocyst counts between experimental mosquito midguts and the control ($p>0.23$), indicating that the polyclonal Ab against human α-tubulin did not prevent *P. falciparum* from invading *An. gambiae* (FIG. 5B). Collectively, these data support that α-tubulin-I is a functional component of the *Plasmodium* invasion machinery and that antibodies directed against α-tubulin-I can function to block *Plasmodium* transmission to mosquitoes.

Example 5—Anti-α-Tubulin Ab does not Affect the Conversion of *P. falciparum* Gametocytes to Ookinetes There is a possibility that the reducing number of oocysts in mosquitoes by Ab might be caused by the lower gametocyte-to-ookinete conversion. To determine this, the purified rabbit polyclonal Ab against human α-tubulin was added into the *P. falciparum* culture containing ~3% gametocytes. The same amount of non-related purified rabbit Ab (anti-V5) was used as a negative control. After incubation, the gametocytes and ookinetes were stained with the Giemsa and examined microscopically. Importantly, the result shows an equivalent number of gametocytes and ookinetes in both the experimental group and the control groups. The ookinete conversion rates (CR, percentage of ookinetes among the total gametocytes) were calculated and ookinete CR in the presence of anti-α-tubulin Ab was 12.8%, while the ookinete CR in the presence of anti-V5 Ab was 12.2% ($p>0.1$, Table 4). Thus, these data support that Ab against human α-tubulin does not affect the conversion of *P. falciparum* gametocytes to ookinetes.

TABLE 4

The effects of antibodies on ookinete conversion

| Polyclonal Antibody | Gametocytemia (%, mean ± sd) | Ookinete Conversion Rate (%, mean ± sd) |
|---|---|---|
| Anti-human α-tubulin | 3.0 ± 0.81 | 12.8 ± 2.9 |
| Anti-V5 | 2.75 ± 0.95 | 12.2 ± 2.7 |

Example 6—Development of Novel Malaria Vaccines Against α-Tubulin-1 from *Plasmodium*

Figure 9A:
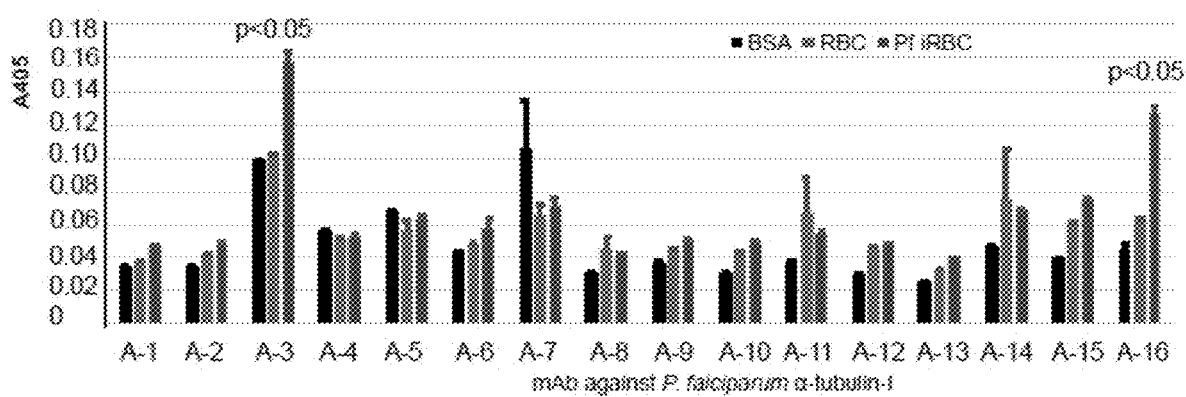
FIGS. 9A-9D show the functional epitopes that can be targeted to block malaria transmission. 9A) ELISA assays of a set of 16 mAb to bind uninfected human red blood cells (RBC), *P. falciparum*-infected human red blood cells (Pf iRBC) and bovine serum album (BSA). 9B) ELISA assays to confirmed mAb that bound to *P. falciparum* α-tubulin-I, but not human α-tubulin. 9C) Standard membrane feeding assays showed mAb against *P. falciparum* α-tubulin-I specifically inhibited *P. falciparum* transmission to *A. gambiae*. 9D) Sequence alignment between human α-tubulin (SEQ ID NO: 1) and *P. falciparum* α-tubulin-I (SEQ ID NO: 5) revealed the functional sequence epitopes (underlined) that were targeted by mAb to block malaria transmission.
Figure 9B:
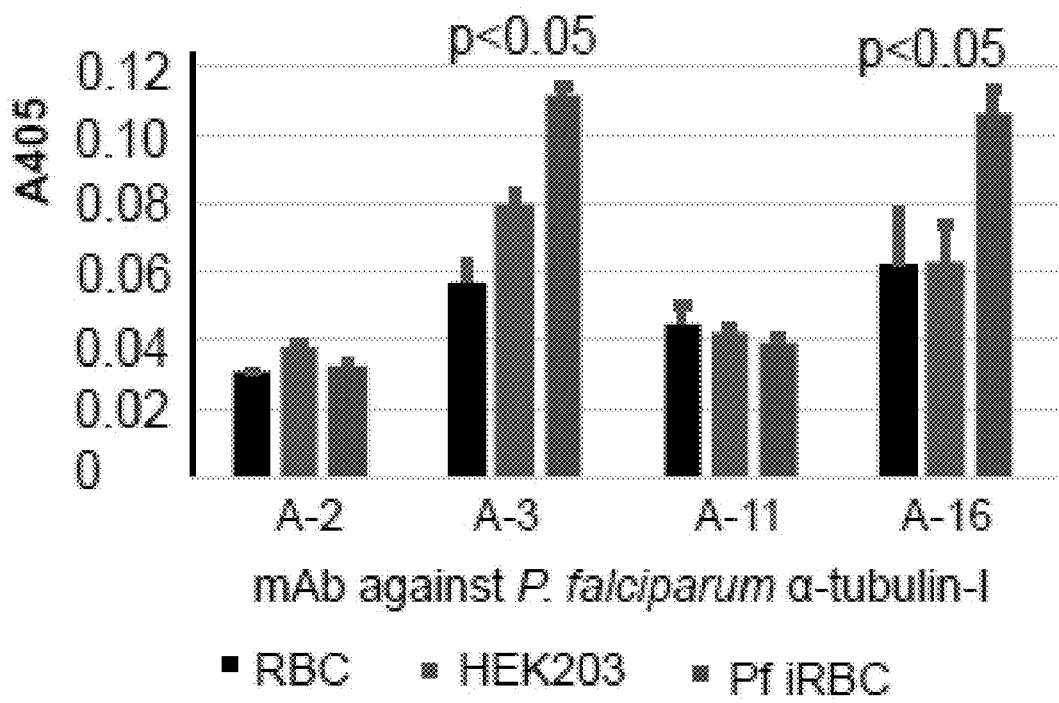
Figure 9C:
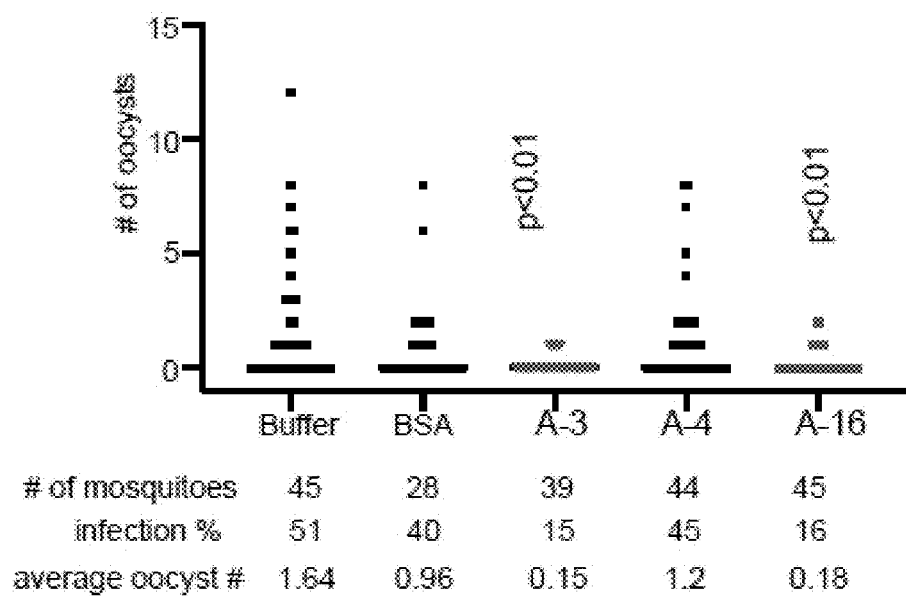
Figure 9D:
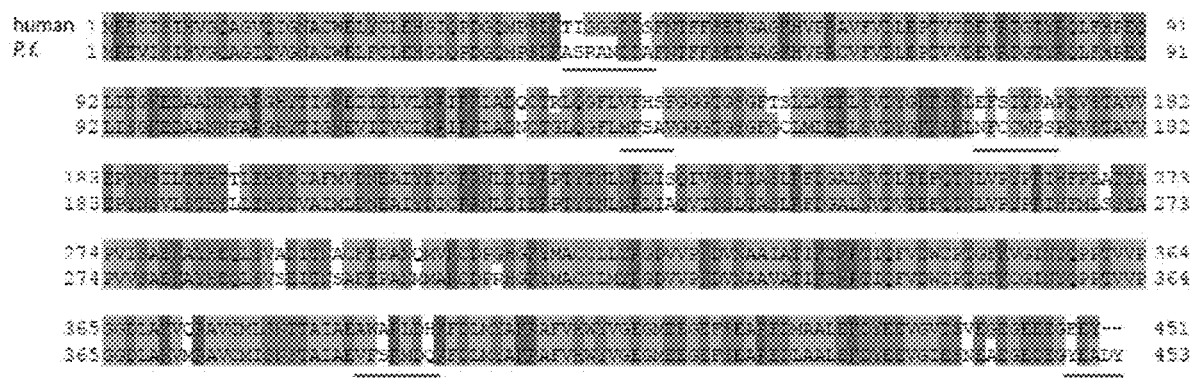

Identifying an unknown binding partner or receptor is always a challenge and the discovery of FBPs is further complicated by the limited source of materials. Less than 5% of *Plasmodium*-infected cells eventually develop into gametocytes, less than 1% of gametocytes become ookinetes. Moreover, a method to separate ookinetes from other cells has not been developed yet. A large amount of non-specific proteins presented in original materials for pull-down assays are expected. The purified insect cell-expressed FREP1-linked magnetic beads were used to reduce pull-down noise. Searching differential mass spectrometry signals against specific *P. berghei* protein database further eliminates non-related proteins. Moreover, most recent Multidimensional Protein Identification approach followed by statistical evaluation provided a short list of reliable candidates. Finally, the candidate genes were cloned and expressed in insect cells, and recombinant proteins were used to confirm the interactions between FREP1 and FBP candidates. Six FBP candidates bound to FREP1, suggesting that FREP1 binds to broad-spectrum of proteins. The interaction between FREP1 and candidate FBPs might be mediated through the protein modification group N-acetylglucosamine, since the fibrinogen-related domain of FREP1 is able to bind to acetylglucosamine on proteins, and two of the six FBP candidates (Hsp70 and α-tubulin 1) have been reported to be O-GlcNAcylated or O-linked β-N-acetylglucosaminylation.

However, α-tubulin-I does not have a signal peptide, indicating that these proteins normally are not cell surface-exposed. To further elucidate cell biological and mechanistic aspects of FREP1-α-tubulin-I interaction that facilitates parasite transmission, IFA was used to examine the localization and accessibility of α-tubulin-I on living ookinetes. Strikingly, anti-α-tubulin Ab bound to the apical end of living ookinetes. The ookinete apical end is the invasive apparatus. Detailed examination of some individual ookinetes supported that anti-α-tubulin Ab bound to the apical ring.

Transmission-blocking assays revealed the direct, consistent, and functional roles of FREP1 and α-tubulin-I. The transmission-blocking and membrane feeding assays in the presence of antigen-specific antibodies show that antiserum against *P. falciparum* α-tubulin-I significantly inhibited *P. falciparum* transmission to *An. gambiae.*

To control for the possible effects of other serum components in blocking transmission, the feeding assays were performed using purified polyclonal rabbit Ab against human α-tubulin. These studies confirmed the functional role of α-tubulin and revealed that anti-α-tubulin antibody significantly reduced *P. falciparum* oocysts in mosquitoes. By comparison, polyclonal antibodies against α-tubulin did not affect *P. falciparum* transmission to mosquitoes at the same condition as the α-tubulin. One argument is that the blocking effects of anti-α-tubulin-I antibodies could be caused by their interference on ookinete formation. To exclude this possibility, whether anti-α-tubulin Ab interfered with ookinete production was examined. The results demonstrated that anti-α-tubulin Ab did not interfere with the gametocyte conversion to ookinetes.

Apicomplexan parasites such as *Plasmodium* parasites and other major human pathogens including *Toxoplasma gondii* and *Cryptosporidium* which are characterized by a subcellular structure called the apical complex where it mediates host penetration and invasion. Microtubules are major cytoskeleton components of apical complex, and α-tubulin-1 is one of major proteins. With transmission electron microscopy, invasive apparatus formed by microtubules have been detected in the apical end of the ookinete. The transmission electron microscope image of a longitudinal ookinete section shows that the apical end of a mature ookinete is extended to form a cone or sucker-like large opening. This structure called invasive apparatus is mainly composed by α-tubulin-1. FREP1 binding α-tubulin 1 might attach an ookinete and orientate an ookinete invasive apparatus toward PM.

Taken together, these data support that α-tubulin-I interacts with FREP1 and facilitates *Plasmodium* ookinetes infecting mosquitoes. These data are consistent with the notion that antibodies in serum can bind and inhibit α-tubulin-I interactions with FREP1 function during parasite invasion of the mosquitoes. Therefore, an ookinete may use the following steps to overcome the physical barrier of PM (FIG. 6). *Anopheles*-expressed FREP1 protein at the midgut PM binds to *Plasmodium* ookinete-expressed α-tubulin-I at the apical end likely the apical polar ring, which anchors and orientates the ookinete invasive apparatus toward the midgut PM. The ookinete secretes digestive enzymes, e.g., including chitinase secreted from the *Plasmodium* invasive apparatus dissolve the chitin and other PM components, to disrupt the integrity of the PM. Final, the parasite penetrates the PM and invades midguts.

Example 7—Identification of Functional Epitopes that can be Targeted to Block Malaria Transmission Since the sequence between human α-tubulin and *P. falciparum* α-tubulin-I shared >84% identical sequences (FIG. 9D), monoclonal antibodies were generated to identify functional epitopes that could be targeted to block malaria transmission. The *P. falciparum* α-tubulin-I and immunize mice were synthesized. Sixteen hybridomas were generated to produce monoclonal antibodies (mAb). Using ELISA, the molecular interaction between mAb and bovine serum album (BSA), and the lysates of uninfected human red blood cells (RBC) and *P. falciparum*-infected human red blood cells (Pf iRBC) showed that two mAb (A-3 and A-16) bound to Pf-iRBC specifically (FIG. 9A). Further analysis between mAb and the lysate of RBC, human kidney cells (HEK203) and Pf iRBC confirmed that the mAb A-3 and A-16 bound to *P. falciparum* α-tubulin-I, but not human α-tubulin (FIG. 9B). Next, the efficiency of mAb in blocking *P. falciparum* transmission to *A. gambiae* was examined by standard membrane assay. Results showed that both A-3 and A-16 mAb (<10 µg/mL) significantly inhibited malaria transmission (FIG. 9C), while mAb A-4 that did not specifically bind to *P. falciparum* did not inhibit malaria transmission. Therefore, the specific functional epitopes (highlighted by red line in FIG. 9D) in *P. falciparum* α-tubulin-I are preferred targets for malaria transmission-blocking vaccines.

In summary, this disclosure describes a FREP1-mediated *Plasmodium* invasion pathway in *Anopheles* midguts and identifies *Plasmodium* α-tubulin 1 as a FREP1 binding partner. Direct interaction between FREP1 and €-tubulin 1 at ookinete invasive apparatus shall position parasite for efficient invasion. In addition, this disclosure also provides targets for malaria control. Malaria transmission-blocking vaccine (TBV) have shown promising perspectives when considering the malaria transmission bottleneck in a mosquito midgut. Both α-tubulin 1 and the FREP1 fibrinogen-like domain are highly conserved (>90% identical) among *Plasmodium* or *Anopheles* species. Thus, they are excellent targets for TBV.

I claim:

1. A method for reducing malaria transmission from a subject through a mosquito, comprising administering to the subject a composition comprising a malaria transmission-blocking agent, the malaria transmission-blocking agent comprising an antibody or antigen binding fragment thereof that specifically binds to YEADY (SEQ ID NO: 7), ASRANDDA (SEQ ID NO: 42), MFSAV (SEQ ID NO: 43), NFCCWPSP (SEQ ID NO: 44), and/or VFSRMDOK (SEQ ID NO: 45) of *Plasmodium* α-tubulin 1.

2. The method according to claim 1, the subject being infected with the malaria parasite.

3. The method according to claim 1, the malarial parasite being *P. berghei, P. vivax, P. knowlesi, P. malariae, P. falciparum*, or *P. ovale*.

4. The method according to claim 1, wherein the antibody or antigen binding fragment thereof blocks the interaction between a mid-gut peritrophic matrix (PM) protein of the mosquito and *Plasmodium* α-tubulin 1.

5. The method according to claim 4, the mid-gut PM protein of the mosquito being FREP-1.

6. The method according to claim 1, the *Plasmodium* α-tubulin-1 comprising a sequence selected from SEQ ID NOs: 2-6 and sequences sharing at least 90% identity to any of SEQ ID NOS: 2-6.

7. A method for blocking the invasion of a malaria parasite from a subject into the midguts of a mosquito, comprising administering to the subject a composition comprising a malaria transmission-blocking agent, the malaria transmission-blocking agent comprising an antibody or antigen binding fragment thereof that specifically binds to YEADY (SEQ ID NO: 7), ASRANDDA (SEQ ID NO: 42), MFSAV (SEQ ID NO: 43), NFCCWPSP (SEQ ID NO: 44), and/or VFSRMDQK (SEQ ID NO: 45) of *Plasmodium* α-tubulin-1.

8. The method according to claim 7, the malarial parasite being *P. berghei, P. vivax, P. knowlesi, P. malariae, P. falciparum*, or *P. ovale*.

9. The method according to claim 7, the *Plasmodium* α-tubulin-1 comprising a sequence selected from SEQ ID NOs: 2-6 and sequences sharing at least 90% identity to any of SEQ ID NOs: 2-6.

10. The method according to claim 7, wherein the subject is infected with malaria.

11. The method according to claim 1, the composition being administered via oral, nasal, intramuscular, subcutaneous, or intravenous administration.

12. The method according to claim 7, the composition being administered via oral, nasal, intramuscular, subcutaneous, or intravenous administration.

13. The method according to claim 1, the antibody or antigen binding fragment thereof specifically binding to SEQ ID NO: 5.

14. The method according to claim 7, the antibody or antigen binding fragment thereof specifically binding to SEQ ID NO: 5.

15. The method according to claim 1, the subject being a mammal.

16. The method according to claim 7, the subject being a mammal.

17. The method according to claim 1, the subject being human.

* * * * *

SEQUENCE LISTING

```
<160> NUMBER OF SEQ ID NOS: 45

<210> SEQ ID NO 1
<211> LENGTH: 451
<212> TYPE: PRT
<213> ORGANISM: Homo sapiens

<400> SEQUENCE: 1

Met Arg Glu Cys Ile Ser Ile His Val Gly Gln Ala Gly Val Gln Val
1               5                   10                  15

Gly Asn Ala Cys Trp Glu Leu Tyr Cys Leu Glu His Gly Ile Gln Pro
            20                  25                  30

Asp Gly Gln Met Pro Ser Asp Lys Thr Ile Gly Gly Gly Asp Asp Ser
        35                  40                  45

Phe Asn Thr Phe Phe Ser Glu Thr Gly Ala Gly Lys His Val Pro Arg
    50                  55                  60

Ala Val Phe Val Asp Leu Glu Pro Thr Val Ile Asp Glu Val Arg Thr
65                  70                  75                  80

Gly Thr Tyr Arg Gln Leu Phe His Pro Glu Gln Leu Ile Thr Gly Lys
                85                  90                  95

Glu Asp Ala Ala Asn Asn Tyr Ala Arg Gly His Tyr Thr Ile Gly Lys
            100                 105                 110

Glu Ile Ile Asp Leu Val Leu Asp Arg Ile Arg Lys Leu Ala Asp Gln
        115                 120                 125

Cys Thr Gly Leu Gln Gly Phe Leu Val Phe His Ser Phe Gly Gly Gly
    130                 135                 140

Thr Gly Ser Gly Phe Thr Ser Leu Leu Met Glu Arg Leu Ser Val Asp
145                 150                 155                 160

Tyr Gly Lys Lys Ser Lys Leu Glu Phe Ser Ile Tyr Pro Ala Pro Gln
                165                 170                 175

Val Ser Thr Ala Val Val Glu Pro Tyr Asn Ser Ile Leu Thr Thr His
            180                 185                 190

Thr Thr Leu Glu His Ser Asp Cys Ala Phe Met Val Asp Asn Glu Ala
        195                 200                 205

Ile Tyr Asp Ile Cys Arg Arg Asn Leu Asp Ile Glu Arg Pro Thr Tyr
    210                 215                 220

Thr Asn Leu Asn Arg Leu Ile Gly Gln Ile Val Ser Ser Ile Thr Ala
225                 230                 235                 240

Ser Leu Arg Phe Asp Gly Ala Leu Asn Val Asp Leu Thr Glu Phe Gln
```

```
            245                 250                 255
Thr Asn Leu Val Pro Tyr Pro Arg Ile His Phe Pro Leu Ala Thr Tyr
            260                 265                 270

Ala Pro Val Ile Ser Ala Glu Lys Ala Tyr His Glu Gln Leu Ser Val
            275                 280                 285

Ala Glu Ile Thr Asn Ala Cys Phe Glu Pro Ala Asn Gln Met Val Lys
            290                 295                 300

Cys Asp Pro Gly His Gly Lys Tyr Met Ala Cys Cys Leu Leu Tyr Arg
305                 310                 315                 320

Gly Asp Val Val Pro Lys Asp Val Asn Ala Ala Ile Ala Thr Ile Lys
                    325                 330                 335

Thr Lys Arg Thr Ile Gln Phe Val Asp Trp Cys Pro Thr Gly Phe Lys
                340                 345                 350

Cys Gly Ile Asn Tyr Gln Pro Pro Thr Val Val Pro Gly Gly Asp Leu
                355                 360                 365

Ala Lys Val Gln Arg Ala Val Cys Met Leu Ser Asn Thr Thr Ala Ile
            370                 375                 380

Ala Glu Ala Trp Ala Arg Leu Asp His Lys Phe Asp Leu Met Tyr Ala
385                 390                 395                 400

Lys Arg Ala Phe Val His Trp Tyr Val Gly Glu Gly Met Glu Glu Gly
                    405                 410                 415

Glu Phe Ser Glu Ala Arg Glu Asp Met Ala Ala Leu Glu Lys Asp Tyr
                420                 425                 430

Glu Glu Val Gly Val His Ser Val Glu Gly Glu Gly Glu Glu Glu Gly
            435                 440                 445

Glu Glu Tyr
        450

<210> SEQ ID NO 2
<211> LENGTH: 453
<212> TYPE: PRT
<213> ORGANISM: Plasmodium vivax

<400> SEQUENCE: 2

Met Arg Glu Val Ile Ser Ile His Val Gly Gln Ala Gly Ile Gln Ile
1               5                   10                  15

Gly Asn Ala Cys Trp Glu Leu Phe Cys Leu Glu His Gly Ile Gln Pro
            20                  25                  30

Asp Gly Gln Met Pro Ser Asp Gln Val Val Ala Gly Gly Asp Asp Ala
        35                  40                  45

Phe Asn Thr Phe Phe Ser Glu Thr Gly Ala Gly Lys His Val Pro Arg
50                  55                  60

Cys Val Phe Val Asp Leu Glu Pro Thr Val Val Asp Glu Val Arg Thr
65                  70                  75                  80

Gly Thr Tyr Arg Gln Leu Phe His Pro Glu Gln Leu Ile Ser Gly Lys
                85                  90                  95

Glu Asp Ala Ala Asn Asn Phe Ala Arg Gly His Tyr Thr Ile Gly Lys
            100                 105                 110

Glu Ile Val Asp Val Cys Leu Asp Arg Val Arg Lys Leu Ala Asp Asn
        115                 120                 125

Cys Thr Gly Leu Gln Gly Phe Leu Met Phe Asn Ala Val Gly Gly Gly
130                 135                 140

Thr Gly Ser Gly Leu Gly Cys Leu Leu Leu Glu Arg Leu Ala Ile Asp
145                 150                 155                 160
```

```
Tyr Gly Lys Lys Ser Lys Leu Asn Phe Cys Ser Trp Pro Ser Pro Gln
            165                 170                 175

Val Ser Thr Ala Val Val Glu Pro Tyr Asn Ser Val Leu Ser Thr His
        180                 185                 190

Ser Leu Leu Glu His Thr Asp Val Ala Ile Met Leu Asp Asn Glu Ala
            195                 200                 205

Ile Tyr Asp Ile Cys Lys Lys Asn Leu Asp Ile Glu Arg Pro Thr Tyr
        210                 215                 220

Thr Asn Leu Asn Arg Leu Ile Ala Gln Val Ile Ser Ser Leu Thr Ala
225                 230                 235                 240

Ser Leu Arg Phe Asp Gly Ala Leu Asn Val Asp Val Thr Glu Phe Gln
            245                 250                 255

Thr Asn Leu Val Pro Tyr Pro Arg Ile His Phe Met Leu Ser Ser Tyr
        260                 265                 270

Ala Pro Ile Ile Ser Ala Glu Lys Ala Tyr His Glu Gln Leu Ser Val
    275                 280                 285

Ser Glu Ile Thr Asn Ser Ala Phe Glu Pro Ala Ser Met Met Ala Lys
    290                 295                 300

Cys Asp Pro Arg His Gly Lys Tyr Met Ala Cys Cys Leu Met Tyr Arg
305                 310                 315                 320

Gly Asp Val Val Pro Lys Asp Val Asn Ala Ala Val Ala Thr Ile Lys
            325                 330                 335

Thr Lys Arg Ser Ile Gln Phe Val Asp Trp Cys Pro Thr Gly Phe Lys
        340                 345                 350

Cys Gly Ile Asn Tyr Gln Pro Pro Thr Val Val Pro Gly Gly Asp Leu
    355                 360                 365

Ala Lys Val Met Arg Ala Val Cys Met Ile Ser Asn Ser Thr Ala Ile
    370                 375                 380

Ala Glu Val Phe Ser Arg Met Asp Gln Lys Phe Asp Leu Met Tyr Ala
385                 390                 395                 400

Lys Arg Ala Phe Val His Trp Tyr Val Gly Glu Gly Met Glu Glu Gly
            405                 410                 415

Glu Phe Ser Glu Ala Arg Glu Asp Leu Ala Ala Leu Glu Lys Asp Tyr
        420                 425                 430

Glu Glu Val Gly Ile Glu Thr Asn Glu Gly Glu Gly Glu Asp Glu Gly
    435                 440                 445

Tyr Glu Ala Asp Tyr
    450

<210> SEQ ID NO 3
<211> LENGTH: 453
<212> TYPE: PRT
<213> ORGANISM: Plasmodium knowlesi

<400> SEQUENCE: 3

Met Arg Glu Val Ile Ser Ile His Val Gly Gln Ala Gly Ile Gln Val
1               5                   10                  15

Gly Asn Ala Cys Trp Glu Leu Phe Cys Leu Glu His Gly Ile Gln Pro
            20                  25                  30

Asp Gly Gln Met Pro Ser Asp Lys Ala Ala Arg Ala Asn Asp Asp Ala
        35                  40                  45

Phe Asn Thr Phe Phe Ser Glu Thr Gly Ala Gly Lys His Val Pro Arg
    50                  55                  60

Cys Val Phe Val Asp Leu Glu Pro Thr Val Val Asp Glu Val Arg Thr
65                  70                  75                  80
```

Gly Thr Tyr Arg Gln Leu Phe His Pro Glu Gln Leu Ile Ser Gly Lys
                85                  90                  95

Glu Asp Ala Ala Asn Asn Phe Ala Arg Gly His Tyr Thr Ile Gly Lys
            100                 105                 110

Glu Val Ile Asp Val Cys Leu Asp Arg Ile Arg Lys Leu Ala Asp Asn
        115                 120                 125

Cys Thr Gly Leu Gln Gly Phe Leu Met Phe Ser Ala Val Gly Gly Gly
    130                 135                 140

Thr Gly Ser Gly Phe Gly Cys Leu Met Leu Glu Arg Leu Ser Val Asp
145                 150                 155                 160

Tyr Gly Lys Lys Ser Lys Leu Asn Phe Cys Cys Trp Pro Ser Pro Gln
                165                 170                 175

Val Ser Thr Ala Val Val Glu Pro Tyr Asn Ser Val Leu Ser Thr His
            180                 185                 190

Ser Leu Leu Glu His Thr Asp Val Ala Ile Met Leu Asp Asn Glu Ala
        195                 200                 205

Ile Tyr Asp Ile Cys Lys Lys Asn Leu Asp Ile Glu Arg Pro Thr Tyr
    210                 215                 220

Thr Asn Leu Asn Arg Leu Ile Ala Gln Val Ile Ser Ser Leu Thr Ala
225                 230                 235                 240

Ser Leu Arg Phe Asp Gly Ala Leu Asn Val Asp Val Thr Glu Phe Gln
                245                 250                 255

Thr Asn Leu Val Pro Tyr Pro Arg Ile His Phe Met Leu Ser Ser Tyr
            260                 265                 270

Ala Pro Val Val Ser Ala Glu Lys Ala Tyr His Glu Gln Leu Ser Val
        275                 280                 285

Ser Glu Ile Thr Asn Ser Ala Phe Glu Pro Ala Asn Met Met Ala Lys
    290                 295                 300

Cys Asp Pro Arg His Gly Lys Tyr Met Ala Cys Cys Leu Met Tyr Arg
305                 310                 315                 320

Gly Asp Val Val Pro Lys Asp Val Asn Ala Ala Val Ala Thr Ile Lys
                325                 330                 335

Thr Lys Arg Thr Ile Gln Phe Val Asp Trp Cys Pro Thr Gly Phe Lys
            340                 345                 350

Cys Gly Ile Asn Tyr Gln Pro Pro Thr Val Val Pro Gly Gly Asp Leu
        355                 360                 365

Ala Lys Val Met Arg Ala Val Cys Met Ile Ser Asn Ser Thr Ala Ile
    370                 375                 380

Ala Glu Val Phe Ser Arg Met Asp Gln Lys Phe Asp Leu Met Tyr Ala
385                 390                 395                 400

Lys Arg Ala Phe Val His Trp Tyr Val Gly Glu Gly Met Glu Glu Gly
                405                 410                 415

Glu Phe Ser Glu Ala Arg Glu Asp Leu Ala Ala Leu Glu Lys Asp Tyr
            420                 425                 430

Glu Glu Val Gly Ile Glu Thr Asn Glu Gly Gly Glu Asp Glu Gly
        435                 440                 445

Tyr Glu Ala Asp Tyr
    450

<210> SEQ ID NO 4
<211> LENGTH: 453
<212> TYPE: PRT
<213> ORGANISM: Plasmodium malariae

<400> SEQUENCE: 4

```
Met Arg Glu Val Ile Ser Ile His Val Gly Gln Ala Gly Ile Gln Val
1               5                   10                  15
Gly Asn Ala Cys Trp Glu Leu Phe Cys Leu Glu His Gly Ile Gln Pro
            20                  25                  30
Asp Gly Gln Met Pro Ser Asp Lys Ala Ala Arg Ala Asn Asp Asp Ala
        35                  40                  45
Phe Asn Thr Phe Phe Ser Glu Thr Gly Ala Gly Lys His Val Pro Arg
50                  55                  60
Cys Val Phe Val Asp Leu Glu Pro Thr Val Val Asp Glu Val Arg Thr
65                  70                  75                  80
Gly Thr Tyr Arg Gln Leu Phe His Pro Glu Gln Leu Ile Ser Gly Lys
                85                  90                  95
Glu Asp Ala Ala Asn Asn Phe Ala Arg Gly His Tyr Thr Ile Gly Lys
            100                 105                 110
Glu Val Ile Asp Val Cys Leu Asp Arg Ile Arg Lys Leu Ala Asp Asn
        115                 120                 125
Cys Thr Gly Leu Gln Gly Phe Leu Met Phe Ser Ala Val Gly Gly Gly
130                 135                 140
Thr Gly Ser Gly Phe Gly Cys Leu Met Leu Glu Arg Leu Ser Val Asp
145                 150                 155                 160
Tyr Gly Lys Lys Ser Lys Leu Asn Phe Cys Cys Trp Pro Ser Pro Gln
                165                 170                 175
Val Ser Thr Ala Val Val Glu Pro Tyr Asn Ser Val Leu Ser Thr His
            180                 185                 190
Ser Leu Leu Glu His Thr Asp Val Ala Ile Met Leu Asp Asn Glu Ala
        195                 200                 205
Ile Tyr Asp Ile Cys Arg Arg Asn Leu Asp Ile Glu Arg Pro Thr Tyr
210                 215                 220
Thr Asn Leu Asn Arg Leu Ile Ala Gln Val Ile Ser Ser Leu Thr Ala
225                 230                 235                 240
Ser Leu Arg Phe Asp Gly Ala Leu Asn Val Asp Val Thr Glu Phe Gln
                245                 250                 255
Thr Asn Leu Val Pro Tyr Pro Arg Ile His Phe Met Leu Ser Ser Tyr
            260                 265                 270
Ala Pro Val Val Ser Ala Glu Lys Ala Tyr His Glu Gln Leu Ser Val
        275                 280                 285
Ser Glu Ile Thr Asn Ser Ala Phe Glu Pro Ala Asn Met Met Ala Lys
290                 295                 300
Cys Asp Pro Arg His Gly Lys Tyr Met Ala Cys Cys Leu Met Tyr Arg
305                 310                 315                 320
Gly Asp Val Val Pro Lys Asp Val Asn Ala Ala Val Ala Thr Ile Lys
                325                 330                 335
Thr Lys Arg Thr Ile Gln Phe Val Asp Trp Cys Pro Thr Gly Phe Lys
            340                 345                 350
Cys Gly Ile Asn Tyr Gln Pro Pro Thr Val Val Pro Gly Gly Asp Leu
        355                 360                 365
Ala Lys Val Met Arg Ala Val Cys Met Ile Ser Asn Ser Thr Ala Ile
370                 375                 380
Ala Glu Val Phe Ser Arg Met Asp Gln Lys Phe Asp Leu Met Tyr Ala
385                 390                 395                 400
Lys Arg Ala Phe Val His Trp Tyr Val Gly Glu Gly Met Glu Glu Gly
                405                 410                 415
```

Glu Phe Ser Glu Ala Arg Glu Asp Leu Ala Ala Leu Glu Lys Asp Tyr
            420                 425                 430

Glu Glu Val Gly Ile Glu Ser Asn Glu Gly Glu Gly Glu Asp Glu Gly
            435                 440                 445

Tyr Asp Gly Asp Tyr
        450

<210> SEQ ID NO 5
<211> LENGTH: 453
<212> TYPE: PRT
<213> ORGANISM: Plasmodium falciparum

<400> SEQUENCE: 5

Met Arg Glu Val Ile Ser Ile His Val Gly Gln Ala Gly Ile Gln Val
1               5                   10                  15

Gly Asn Ala Cys Trp Glu Leu Phe Cys Leu Glu His Gly Ile Gln Pro
            20                  25                  30

Asp Gly Gln Met Pro Ser Asp Lys Ala Ser Arg Ala Asn Asp Asp Ala
        35                  40                  45

Phe Asn Thr Phe Phe Ser Glu Thr Gly Ala Gly Lys His Val Pro Arg
    50                  55                  60

Cys Val Phe Val Asp Leu Glu Pro Thr Val Val Asp Glu Val Arg Thr
65                  70                  75                  80

Gly Thr Tyr Arg Gln Leu Phe His Pro Glu Gln Leu Ile Ser Gly Lys
                85                  90                  95

Glu Asp Ala Ala Asn Asn Phe Ala Arg Gly His Tyr Thr Ile Gly Lys
            100                 105                 110

Glu Val Ile Asp Val Cys Leu Asp Arg Ile Arg Lys Leu Ala Asp Asn
        115                 120                 125

Cys Thr Gly Leu Gln Gly Phe Leu Met Phe Ser Ala Val Gly Gly Gly
    130                 135                 140

Thr Gly Ser Gly Phe Gly Cys Leu Met Leu Glu Arg Leu Ser Val Asp
145                 150                 155                 160

Tyr Gly Lys Lys Ser Lys Leu Asn Phe Cys Cys Trp Pro Ser Pro Gln
                165                 170                 175

Val Ser Thr Ala Val Val Glu Pro Tyr Asn Ser Val Leu Ser Thr His
            180                 185                 190

Ser Leu Leu Glu His Thr Asp Val Ala Ile Met Leu Asp Asn Glu Ala
        195                 200                 205

Ile Tyr Asp Ile Cys Arg Arg Asn Leu Asp Ile Glu Arg Pro Thr Tyr
    210                 215                 220

Thr Asn Leu Asn Arg Leu Ile Ala Gln Val Ile Ser Ser Leu Thr Ala
225                 230                 235                 240

Ser Leu Arg Phe Asp Gly Ala Leu Asn Val Asp Val Thr Glu Phe Gln
                245                 250                 255

Thr Asn Leu Val Pro Tyr Pro Arg Ile His Phe Met Leu Ser Ser Tyr
            260                 265                 270

Ala Pro Val Val Ser Ala Glu Lys Ala Tyr His Glu Gln Leu Ser Val
        275                 280                 285

Ser Glu Ile Thr Asn Ser Ala Phe Glu Pro Ala Asn Met Met Ala Lys
    290                 295                 300

Cys Asp Pro Arg His Gly Lys Tyr Met Ala Cys Cys Leu Met Tyr Arg
305                 310                 315                 320

Gly Asp Val Val Pro Lys Asp Val Asn Ala Ala Val Ala Thr Ile Lys

```
                    325                 330                 335
Thr Lys Arg Thr Ile Gln Phe Val Asp Trp Cys Pro Thr Gly Phe Lys
            340                 345                 350
Cys Gly Ile Asn Tyr Gln Pro Pro Thr Val Val Pro Gly Gly Asp Leu
        355                 360                 365
Ala Lys Val Met Arg Ala Val Cys Met Ile Ser Asn Ser Thr Ala Ile
370                 375                 380
Ala Glu Val Phe Ser Arg Met Asp Gln Lys Phe Asp Leu Met Tyr Ala
385                 390                 395                 400
Lys Arg Ala Phe Val His Trp Tyr Val Gly Glu Gly Met Glu Glu Gly
                405                 410                 415
Glu Phe Ser Glu Ala Arg Glu Asp Leu Ala Ala Leu Glu Lys Asp Tyr
            420                 425                 430
Glu Glu Val Gly Ile Glu Ser Asn Glu Ala Glu Gly Glu Asp Glu Gly
        435                 440                 445
Tyr Glu Ala Asp Tyr
    450

<210> SEQ ID NO 6
<211> LENGTH: 453
<212> TYPE: PRT
<213> ORGANISM: Plasmodium ovale

<400> SEQUENCE: 6

Met Arg Glu Val Ile Ser Ile His Val Gly Gln Ala Gly Ile Gln Val
1               5                   10                  15
Gly Asn Ala Cys Trp Glu Leu Phe Cys Leu Glu His Gly Ile Gln Pro
            20                  25                  30
Asp Gly Gln Met Pro Ser Asp Lys Ala Ala Arg Ala Asn Asp Asp Ala
        35                  40                  45
Phe Asn Thr Phe Phe Ser Glu Thr Gly Ala Gly Lys His Val Pro Arg
    50                  55                  60
Cys Val Phe Val Asp Leu Glu Pro Thr Val Val Asp Glu Val Arg Thr
65                  70                  75                  80
Gly Thr Tyr Arg Gln Leu Phe His Pro Glu Gln Leu Ile Ser Gly Lys
                85                  90                  95
Glu Asp Ala Ala Asn Asn Phe Ala Arg Gly His Tyr Thr Ile Gly Lys
            100                 105                 110
Glu Val Ile Asp Val Cys Leu Asp Arg Ile Arg Lys Leu Ala Asp Asn
        115                 120                 125
Cys Thr Gly Leu Gln Gly Phe Leu Met Phe Ser Ala Val Gly Gly Gly
    130                 135                 140
Thr Gly Ser Gly Phe Gly Cys Leu Met Leu Glu Arg Leu Ser Val Asp
145                 150                 155                 160
Tyr Gly Lys Lys Ser Lys Leu Asn Phe Cys Cys Trp Pro Ser Pro Gln
                165                 170                 175
Val Ser Thr Ala Val Val Glu Pro Tyr Asn Ser Val Leu Ser Thr His
            180                 185                 190
Ser Leu Leu Glu His Thr Asp Val Ala Ile Met Leu Asp Asn Glu Ala
        195                 200                 205
Ile Tyr Asp Ile Cys Arg Arg Asn Leu Asp Ile Glu Arg Pro Thr Tyr
    210                 215                 220
Thr Asn Leu Asn Arg Leu Ile Ala Gln Val Ile Ser Ser Leu Thr Ala
225                 230                 235                 240
```

```
Ser Leu Arg Phe Asp Gly Ala Leu Asn Val Asp Val Thr Glu Phe Gln
            245                 250                 255

Thr Asn Leu Val Pro Tyr Pro Arg Ile His Phe Met Leu Ser Ser Tyr
        260                 265                 270

Ala Pro Val Val Ser Ala Glu Lys Ala Tyr His Glu Gln Leu Ser Val
    275                 280                 285

Ser Glu Ile Thr Asn Ser Ala Phe Glu Pro Ala Asn Met Met Ala Lys
290                 295                 300

Cys Asp Pro Arg His Gly Lys Tyr Met Ala Cys Cys Leu Met Tyr Arg
305                 310                 315                 320

Gly Asp Val Val Pro Lys Asp Val Asn Ala Ala Val Ala Thr Ile Lys
                325                 330                 335

Thr Lys Arg Thr Ile Gln Phe Val Asp Trp Cys Pro Thr Gly Phe Lys
            340                 345                 350

Cys Gly Ile Asn Tyr Gln Pro Pro Thr Val Val Pro Gly Gly Asp Leu
        355                 360                 365

Ala Lys Val Met Arg Ala Val Cys Met Ile Ser Asn Ser Thr Ala Ile
    370                 375                 380

Ala Glu Val Phe Ser Arg Met Asp Gln Lys Phe Asp Leu Met Tyr Ala
385                 390                 395                 400

Lys Arg Ala Phe Val His Trp Tyr Val Gly Glu Gly Met Glu Glu Gly
                405                 410                 415

Glu Phe Ser Glu Ala Arg Glu Asp Leu Ala Ala Leu Glu Lys Asp Tyr
            420                 425                 430

Glu Glu Val Gly Ile Glu Ser Asn Glu Gly Gly Gly Asp Glu Gly
        435                 440                 445

Tyr Glu Ala Asp Tyr
    450

<210> SEQ ID NO 7
<211> LENGTH: 5
<212> TYPE: PRT
<213> ORGANISM: Plasmodium falciparum

<400> SEQUENCE: 7

Tyr Glu Ala Asp Tyr
1               5

<210> SEQ ID NO 8
<211> LENGTH: 9
<212> TYPE: PRT
<213> ORGANISM: Plasmodium knowlesi

<400> SEQUENCE: 8

Ala Ala Arg Ala Asn Asp Asp Ala Phe
1               5

<210> SEQ ID NO 9
<211> LENGTH: 5
<212> TYPE: PRT
<213> ORGANISM: Plasmodium knowlesi

<400> SEQUENCE: 9

Ala Ala Arg Ala Asn
1               5

<210> SEQ ID NO 10
<211> LENGTH: 6
<212> TYPE: PRT
```

```
<213> ORGANISM: Plasmodium vivax

<400> SEQUENCE: 10

Gln Val Val Ala Gly Gly
1               5

<210> SEQ ID NO 11
<211> LENGTH: 10
<212> TYPE: PRT
<213> ORGANISM: Plasmodium vivax

<400> SEQUENCE: 11

Gln Val Val Ala Gly Gly Asp Asp Ala Phe
1               5                   10

<210> SEQ ID NO 12
<211> LENGTH: 13
<212> TYPE: PRT
<213> ORGANISM: Plasmodium falciparum

<400> SEQUENCE: 12

Ser Thr His Ser Leu Leu Glu His Thr Asp Val Ala Ile
1               5                   10

<210> SEQ ID NO 13
<211> LENGTH: 5
<212> TYPE: PRT
<213> ORGANISM: Plasmodium vivax

<400> SEQUENCE: 13

Ile Glu Thr Asn Glu
1               5

<210> SEQ ID NO 14
<211> LENGTH: 9
<212> TYPE: PRT
<213> ORGANISM: Plasmodium falciparum

<400> SEQUENCE: 14

Ala Ser Arg Ala Asn Asp Asp Ala Phe
1               5

<210> SEQ ID NO 15
<211> LENGTH: 5
<212> TYPE: PRT
<213> ORGANISM: Plasmodium falciparum

<400> SEQUENCE: 15

Ala Ser Arg Ala Asn
1               5

<210> SEQ ID NO 16
<211> LENGTH: 12
<212> TYPE: PRT
<213> ORGANISM: Plasmodium falciparum

<400> SEQUENCE: 16

Ala Glu Val Phe Ser Arg Met Asp Gln Lys Phe Asp
1               5                   10

<210> SEQ ID NO 17
<211> LENGTH: 14
<212> TYPE: PRT
<213> ORGANISM: Plasmodium falciparum
```

```
<400> SEQUENCE: 17

Phe Gly Cys Leu Met Leu Glu Arg Leu Ser Val Asp Tyr Gly
1               5                   10

<210> SEQ ID NO 18
<211> LENGTH: 8
<212> TYPE: PRT
<213> ORGANISM: Homo sapiens

<400> SEQUENCE: 18

Thr Ile Gly Gly Gly Asp Asp Ser
1               5

<210> SEQ ID NO 19
<211> LENGTH: 5
<212> TYPE: PRT
<213> ORGANISM: Homo sapiens

<400> SEQUENCE: 19

Thr Ile Gly Gly Gly
1               5

<210> SEQ ID NO 20
<211> LENGTH: 27
<212> TYPE: DNA
<213> ORGANISM: Artificial sequence
<220> FEATURE:
<223> OTHER INFORMATION: primer

<400> SEQUENCE: 20
cgggatccat gaagaaagga aataacg                                        27

<210> SEQ ID NO 21
<211> LENGTH: 25
<212> TYPE: DNA
<213> ORGANISM: Artificial sequence
<220> FEATURE:
<223> OTHER INFORMATION: primer

<400> SEQUENCE: 21
cgctcgagca taggttttgc tctac                                          25

<210> SEQ ID NO 22
<211> LENGTH: 30
<212> TYPE: DNA
<213> ORGANISM: Artificial sequence
<220> FEATURE:
<223> OTHER INFORMATION: primer

<400> SEQUENCE: 22
cgggatccat gccgcaatgg gggactggta                                     30

<210> SEQ ID NO 23
<211> LENGTH: 28
<212> TYPE: DNA
<213> ORGANISM: Artificial sequence
<220> FEATURE:
<223> OTHER INFORMATION: primer

<400> SEQUENCE: 23
gctctagaat cctttgatt cattgggt                                        28

<210> SEQ ID NO 24
<211> LENGTH: 30
<212> TYPE: DNA
```

```
<213> ORGANISM: Artificial sequence
<220> FEATURE:
<223> OTHER INFORMATION: primer

<400> SEQUENCE: 24
cgggatccat gagagaagta ataagtatac                                        30

<210> SEQ ID NO 25
<211> LENGTH: 29
<212> TYPE: DNA
<213> ORGANISM: Artificial sequence
<220> FEATURE:
<223> OTHER INFORMATION: primer

<400> SEQUENCE: 25
gctctagaat agtctgcctc atatccttc                                         29

<210> SEQ ID NO 26
<211> LENGTH: 30
<212> TYPE: DNA
<213> ORGANISM: Artificial sequence
<220> FEATURE:
<223> OTHER INFORMATION: primer

<400> SEQUENCE: 26
cgggatccat ggaagaaatg cgatcattac                                        30

<210> SEQ ID NO 27
<211> LENGTH: 30
<212> TYPE: DNA
<213> ORGANISM: Artificial sequence
<220> FEATURE:
<223> OTHER INFORMATION: primer

<400> SEQUENCE: 27
gctctagatc gtcgtctact ggatcgattc                                        30

<210> SEQ ID NO 28
<211> LENGTH: 30
<212> TYPE: DNA
<213> ORGANISM: Artificial sequence
<220> FEATURE:
<223> OTHER INFORMATION: primer

<400> SEQUENCE: 28
cgggatccat gaaaggtttt aataattttc                                        30

<210> SEQ ID NO 29
<211> LENGTH: 28
<212> TYPE: DNA
<213> ORGANISM: Artificial sequence
<220> FEATURE:
<223> OTHER INFORMATION: primer

<400> SEQUENCE: 29
gctctagagt aatatttatt tccgcctc                                          28

<210> SEQ ID NO 30
<211> LENGTH: 30
<212> TYPE: DNA
<213> ORGANISM: Artificial sequence
<220> FEATURE:
<223> OTHER INFORMATION: primer

<400> SEQUENCE: 30
cgggatccat ggctaacgca aaagcaaagc                                        30
```

<210> SEQ ID NO 31
<211> LENGTH: 31
<212> TYPE: DNA
<213> ORGANISM: Artificial sequence
<220> FEATURE:
<223> OTHER INFORMATION: primer

<400> SEQUENCE: 31
gctctagaat caacttcttc aacagttggt c                          31

<210> SEQ ID NO 32
<211> LENGTH: 29
<212> TYPE: DNA
<213> ORGANISM: Artificial sequence
<220> FEATURE:
<223> OTHER INFORMATION: primer

<400> SEQUENCE: 32
cgggatccat gaaagctgct aaaaatgag                             29

<210> SEQ ID NO 33
<211> LENGTH: 25
<212> TYPE: DNA
<213> ORGANISM: Artificial sequence
<220> FEATURE:
<223> OTHER INFORMATION: primer

<400> SEQUENCE: 33
gctctagatt cattctttt cacag                                  25

<210> SEQ ID NO 34
<211> LENGTH: 29
<212> TYPE: DNA
<213> ORGANISM: Artificial sequence
<220> FEATURE:
<223> OTHER INFORMATION: primer

<400> SEQUENCE: 34
cgggatccat gggaaaagaa aaaactcac                             29

<210> SEQ ID NO 35
<211> LENGTH: 29
<212> TYPE: DNA
<213> ORGANISM: Artificial sequence
<220> FEATURE:
<223> OTHER INFORMATION: primer

<400> SEQUENCE: 35
gctctagatt ttttgctgg tgctttagc                              29

<210> SEQ ID NO 36
<211> LENGTH: 30
<212> TYPE: DNA
<213> ORGANISM: Artificial sequence
<220> FEATURE:
<223> OTHER INFORMATION: primer

<400> SEQUENCE: 36
cggaattcat ggcaaaaatt acaaaaatcg                            30

<210> SEQ ID NO 37
<211> LENGTH: 32
<212> TYPE: DNA
<213> ORGANISM: Artificial sequence
<220> FEATURE:

<223> OTHER INFORMATION: primer

<400> SEQUENCE: 37
gctctagatt cacccatttt attaaatcct tc                               32

<210> SEQ ID NO 38
<211> LENGTH: 30
<212> TYPE: DNA
<213> ORGANISM: Artificial sequence
<220> FEATURE:
<223> OTHER INFORMATION: primer

<400> SEQUENCE: 38
cgggatccat ggctaacgca aaagcaaagc                                  30

<210> SEQ ID NO 39
<211> LENGTH: 35
<212> TYPE: DNA
<213> ORGANISM: Artificial sequence
<220> FEATURE:
<223> OTHER INFORMATION: primer

<400> SEQUENCE: 39
cgcaagcttt taatcaactt cttcaacagt tggtc                            35

<210> SEQ ID NO 40
<211> LENGTH: 30
<212> TYPE: DNA
<213> ORGANISM: Artificial sequence
<220> FEATURE:
<223> OTHER INFORMATION: primer

<400> SEQUENCE: 40
cgggatccat gagagaagta ataagtatac                                  30

<210> SEQ ID NO 41
<211> LENGTH: 29
<212> TYPE: DNA
<213> ORGANISM: Artificial sequence
<220> FEATURE:
<223> OTHER INFORMATION: primer

<400> SEQUENCE: 41
gctctagaat agtctgcctc atatccttc                                   29

<210> SEQ ID NO 42
<211> LENGTH: 8
<212> TYPE: PRT
<213> ORGANISM: Plasmodium falciparum

<400> SEQUENCE: 42

Ala Ser Arg Ala Asn Asp Asp Ala
1               5

<210> SEQ ID NO 43
<211> LENGTH: 5
<212> TYPE: PRT
<213> ORGANISM: Plasmodium falciparum

<400> SEQUENCE: 43

Met Phe Ser Ala Val
1               5

<210> SEQ ID NO 44
<211> LENGTH: 8

```
<212> TYPE: PRT
<213> ORGANISM: Plasmodium falciparum

<400> SEQUENCE: 44

Asn Phe Cys Cys Trp Pro Ser Pro
1               5

<210> SEQ ID NO 45
<211> LENGTH: 8
<212> TYPE: PRT
<213> ORGANISM: Plasmodium falciparum

<400> SEQUENCE: 45

Val Phe Ser Arg Met Asp Gln Lys
1               5
```